US006632634B1

(12) United States Patent
Caras et al.

(10) Patent No.: US 6,632,634 B1
(45) Date of Patent: *Oct. 14, 2003

(54) DECAY ACCELERATING FACTOR (DAF) AND NUCLEIC ACID ENCODING IT

(75) Inventors: Ingrid W. Caras, San Francisco, CA (US); Michael A. Davitz, Bronx, NY (US); Victor Nussenzweig, New York, NY (US); David W. Martin, Jr., San Francisco, CA (US)

(73) Assignee: Genentech, Inc., South San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/014,240

(22) Filed: Jan. 27, 1998

Related U.S. Application Data

(63) Continuation of application No. 08/358,283, filed on Dec. 19, 1994, now Pat. No. 5,763,224, which is a continuation of application No. 08/017,934, filed on Feb. 12, 1993, now Pat. No. 5,324,548, which is a continuation-in-part of application No. 07/811,048, filed on Dec. 19, 1991, now Pat. No. 5,264,357, which is a division of application No. 07/083,757, filed on Aug. 6, 1987, now Pat. No. 5,109,113, which is a continuation-in-part of application No. 06/859,107, filed on May 1, 1986, now abandoned, which is a continuation-in-part of application No. 06/738,171, filed on May 24, 1985, now abandoned.

(51) Int. Cl.$^7$ .............................................. C07H 21/04
(52) U.S. Cl. ................... 435/69.1; 435/325; 435/252.3; 435/69.7; 435/320.1; 536/23.5
(58) Field of Search ....................... 530/350; 536/23.5; 435/69.1, 325, 252.3, 69.7, 320.1; 935/9

(56) References Cited

U.S. PATENT DOCUMENTS

| | | | |
|---|---|---|---|
| 3,993,754 A | 11/1976 | Rahman et al. |
| 4,480,041 A | 10/1984 | Myles et al. |
| 4,675,285 A | 6/1987 | Clark et al. |
| 4,687,661 A | 8/1987 | Kikuchi et al. |
| 5,109,113 A | 4/1992 | Caras et al. |
| 5,212,071 A | 5/1993 | Fearon et al. |
| 5,223,394 A | 6/1993 | Wallner |
| 5,264,357 A | 11/1993 | Caras et al. |
| 5,374,548 A | 12/1994 | Caras |
| 5,763,224 A | 6/1998 | Caras et al. |

FOREIGN PATENT DOCUMENTS

| EP | WO 86/07062 | 12/1986 |
|---|---|---|
| EP | 244267 A2 | 4/1987 |

OTHER PUBLICATIONS

American Type Culture Collection *ATCC Catalogue of Cell Lines & Hybridomas*, 7th edition, Rockville, Maryland:American Type Culture Collection pp. 4 (1992).

Anderson et al., "Isolation of a Genomic Clone for Bovine Pancreatic Trypsin Inhibitor by Using a Unique–Sequence Synthetic DNA Probe" *Proc. Natl. Acad. Sci, USA* 80:6838–6842 (1983).

Barnstable et al., "Production of Monoclonal Antibodies to Group A Erythrocytes, HLA and Other Human Cell Surface Antigens—New Tools for Genetic Analysis" *Cell* 14(5):9–20 (May 1978).

Bhown et al., "The Use of HPLC in Protein Sequencing" *CRC Handbook of HPLC for the Separation of Amino Acids, Peptides and Proteins* 2:267–278 (1984).

Brodsky et al., "Monoclonal Antibodies for Analysis of the HLA System" *Immunological Reviews* 47:3–61 (1979).

Caras et al., "Analysis of the Signal Attachment of a Glycophospholipid Membrane Anchor" *Journal of Cell Biology* 108:1387–1396 (1989).

Caras et al., "cDNA Cloning of Decay Accerlerating Factor Reveals Novel Use of Splicing to Generate Two Protein Forms" *Molecular Genetics of Complement Workshop* (MIT/Endicott House, Boston,MA.Oct. 18–20) (1986).

Caras et al., "Cloning of decay–accelating factor suggests novel use of splicing to generate two proteins" *Nature* 325:545–549 (Feb. 1987).

Caras et al., "Signal for Attachment of a Phospholipid Membrane Anchor in Decay Accelerating Factor" *Science* 238:1280–1283 (1987).

Clonis, Y., "Large–scale Affinity Chromatography" *Bio/Technology* 5:1290–1293 (Dec. 1987).

Cross, G.A.M., "Eukaryotic protein modification and membrane attachment via phosphatidylinositol" *Cell* 48:179–181 (1987).

Cross, G.A.M., "Structure of the variant glycoproteins and surface coat of *Trypanosoma brucei*" *Philos. Trans. R. Soc. London* 307(Ser. B):3–12 (1984).

Darnell et al., "Macromolecules in Prokaryotic and Eukaryotic Cells" *Molecular Cell Biology*, Scientific American Books pp. 136 (1986).

Davitz et al., "Isolation of Decay Accelerating Factor (DAF) By a Two–step Procedure and Determination of Its N–terminal Sequence" *Journal of Immunological Methods* 97:71–76 (1987).

(List continued on next page.)

*Primary Examiner*—Lorraine Spector
(74) *Attorney, Agent, or Firm*—Ginger R. Dreger; Heller Ehrman White & McAuliffe LLP

(57) ABSTRACT

Novel fusions of a GPI signal domain and a polypeptide heterologous to the GPI signal domain donor polypeptide are provided for industrial use. Therapeutic administration of the GPI-linked product of the fusions enables the targeting of biological activity to cell membrane surfaces.

22 Claims, 17 Drawing Sheets

OTHER PUBLICATIONS

Davitz et al., "Release of decay–accelerating factor (DAF) from the cell membrane by phosphatidylinositol–specific phospholipase C (PIPLC)" *Journal of Experimental Medicine* 163:1150–1161 (1986).

Dizdaroglu et al., "Comparison of Reversed–Phase and Weak Anion–Exchange High–Performance Liquid Chromatographic Methods for Peptide Separations" *Journal of Chromatography* 264:223–229 (1983).

Fearon, "Regulation of the amplification C3 convertase of human complement by an inhibitory protein isolated from human erythrocyte membrane" *Proc. Natl. Acad. Sci. USA* 76(11):5867–5871 (Nov. 1979).

Ferguson et al., "Glycosyl–sn–1,2–dimyristylphosphatidylinositol Is Covalently Linked to *Trypanosoma brucei* Variant Surface Glycoprotein" *Journal of Biological Chemistry* 260(27):14547–14555 (1985).

Futerman et al., "Physicochemical behaviour and structural characteristics of membrane–bound acetylcholinesterase from Torpedo electric organ. Effect of phosphatidylinositol–specific phospholipase C" *Biochemical Journal* 226(2):369–377 (1985).

Gahmberg et al., "Expression of the Major Sialoglycoprotein (Glycophorin) on Erythroid Cells in Human Bone Marrow" *Blood* 52(2):379–387 (1978).

Glover, D., "The Principles of Cloning DNA" *Gene Cloning: The Mechanics of DNA Manipulation,* Second edition, New York:Chapman and Hall pp. 1–20 (1980).

Grantham et al., "Codon Catalog Usage is a Genome Strategy Modulated for Gene Expressivity" *Nucleic Acids Research* 9(1):r43–r74 (1981).

Gubler et al., "A Simple and Very Efficient Method for Generating cDNA Libraries" *Gene* 25:263–269 (1983).

Hewick et al., "A Gas–Liquid Solid Phase Peptide and Protein Sequenator" *The Journal of Biological Chemistry* 256(15):7990–7997 (1981).

Hoffmann, E., "Inhibition of Complement by A Substance Isolated From Human Erythrocytes–I. Extraction from Human Erythrocyte Stromata" *Immunochemistry* 6:391–403 (1969).

Hoffmann, E., "Inhibition of Complement By A Substance Isolated From Human Erythrocytes–II. Studies on the Site and Mechanism of Action" *Immunochemistry* 6:405–419 (1969).

Holers et al., "Human C3b– and C4b–regulatory proteins: a new multi–gene family" *Immunology Today* 6(6):188–192 (1985).

Hunkapiller et al., "Isolation of Microgram Quantities of Proteins From Polyacrylamide Gels for Amino Acid Sequence Analysis" *Methods In Enzymology* 91:227–236 (1983).

Iida et al., "Complement Receptor ($CR_1$) Deficiency in Erythrocytes from Patients with Systemic Lupus Erythematosus" *Journal of Experimental Medicine* 155:1427–1438 (May 1982).

Iida et al., "Complement Receptor is an Inhibitor of the Complement Cascade" *Journal of Experimental Medicine* 153:1138–1150 (May 1981).

Jacobs et al., "Isolation and Characterization of Genomic and cDNA Clones of Human Erythropoietin" *Nature* 313:806–810 (Feb. 1985).

Johnstone et al. *Immunochemistry In Practice,* Blackwell Scientific Publications pp. 210–211 (1982).

Kam et al., "Cloning, Sequencing and Chromosomal Localization of Human Term Placental Alkaline Phosphatase cDNA" *Proc. Natl. Acad. Sci. USA* 82:8715–8719 (Dec. 1985).

Kinoshita et al., "Distribution of Decay–Accelerating Factor in the Peripheral Blood of Normal Individuals and Patients with Paroxysmal Nocturnal Hemoglobinuria" *Journal of Experimental Medicine* 162:75–92 (1985).

Kunkel, T., "Rapid and Efficient Site–Specific Mutagenesis Without Phenotypic Selection" *Proc. Natl. Acad. Sci.* 82:488–492 (1985).

Lathe, R., "Synthetic Oligonucleotide Probes Deduced from Amino Acid Sequence Data: Theoretical and Practical Considerations" *Journal of Molecular Biology* 183(1):1–12 (May 5, 1985).

Leonard et al., "Molecular cloning and expression of cDNAs for the human interleukin–2 receptor" *Nature* 311:626–631 (Oct. 1984).

Lingappa et al., "Determinants for Protein Localization: β–Lactamase Signal Sequence Directs Globin Across Microsomal Membranes" *Proc. Natl. Acad. Sci. USA* 81:456–460 (1984).

Low & Finean, "Specific release of plasma membrane enzymes by a phosphatidylinositol–specific phospholipase C" *Biochimica et Biophysica Acta* 508:565–570 (1978).

Low et al., "Phosphatidylinositol is the membrane–anchoring domain of the Thy–1 glycoprotein" *Nature* 318:62–64 (1985).

Low MG, "Biochemistry of the glycosyl–phosphatidylinositol membrane protein anchors" *Biochemical Journal* 244(1):1–13 (1987).

Low, M.G. et al., "Covalently attached phosphatidylinositol as a hydrophobic anchor for membrane proteins" *TIBS* 11:212–215 (1986).

Lublin & Atkinson, "Decay–Accelerating Factor:Biochemistry, Molecular Biology, and Function" *Ann. Rev. Immunol.* 7:35–58 (1989).

Lublin et al., "Biosynthesis and Glycosylation of Decay–Accelerating Factor" *Complement* (abstract #140 from the XIth International Complement Workshop held Nov. 3–5, 1985 in Miami, FL) 2:49–50 (1985).

Lublin et al., "Biosynthesis and Glycosylation of the Human Complement Regulatory Protein Decay–Accelerating Factor" *Journal of Immunology* 137(5):1629–1635 (1986).

Lublin et al., "Cloning and Characterization of cDNAs Encoding the Complete Sequence of Decay Accelerating Factor of Human Complement" *Molecular Genetics of Complement Workshop* (MIT/Endicott House, Boston,MA. Oct. 18–20) (1986).

Lublin, D., "Declaration of Douglas M. Lublin" (In the Matter of EP 0,244,267) pp. 1–20, 1–7 (Oct. 18, 1996).

Maniatis et al. *Molecular Cloning: A Laboratory Manual,* New York:Cold Spring Harbor Laboratory pp. 31, 90–91, 133–134 (1982).

Medicus et al., "Role of human factor I and C3b receptor in he cleavage of surface–bound C3bi molecules" *European Journal of Immunology* 13:465–470 (1983).

Medof et al., "Amelioration of Lytic Abnormalities of Paroxysmal Nocturnal Hemoglobinuria with Decay–Accelerating Factor" *Proc. Natl. Acad. Sci.* 82:2980–2984 (1985).

Medof et al., "Cloning and characterization of cDNAS encoding the complete sequence of decay–accelerating factor of human complement" *Proc. Natl. Acad. Sci. USA* 84:2007–2011 (1987).

Medof et al., "Control of the Function of Substrate–Bound C4b–C3b by the Complement Receptor CR1" *Journal of Experimental Medicine* 159:1669–85 (Jun. 1984).

Medof et al., "Decay Accelerating Factor of Complement is Anchored to Cells by a C–Terminal Glycolipid" *Biochemistry* 25:6740–6747 (1986).

Medof et al., "Identification of the Complement Decay–Accelerating Factor (DAF) on Epithelium and Glandular Cells and in Body Fluids" *Journal of Experimental Medicine* 165:848–864 (1987).

Medof et al., "Inhibition of Complement Activation on the Surface of Cells After Incorporation of Decay–Accelerating Factor (DAF) into their Membranes" *Journal of Experimental Medicine* 160:1558–1578 (Nov. 1984).

Medof et al., "Unique Role of the Complement Receptor $CR_1$ in the Degradation of C3b Associated with Immune Complexes" *Journal of Experimental Medicine* 156:1739–1754 (Dec. 1982).

Medof et al., "Variants of DAF on Epithelial Cell Surfaces and In Extracellular Fluids" *Complement* (abstract #151 from the XIth International Complement Workshop held Nov. 3–5, 1985 in Miami, FL) 2:53–54 (1985).

Miyakawa et al., "Defective Immune–Adherence (C3b) Receptor on Erythrocytes from Patients with Systemic Lupus Erythematosus" *Lancet* 2:493–497 (Sep. 1981).

Moran et al., "Fusion of Sequence Elements from Non–anchored Proteins to Generate a Fully Functional Signal for Glycophosphatidylinositol Membrane Anchor Attachment" *Journal of Cell Biology* 115(6):1595–1600 (Dec. 1991).

Moran et al., "Glycophospholipid membrane anchor attachment. Molecular analysis of the cleavage/attachment site" *Journal of Biological Chemistry* 266(2):1250–1257 (Jan. 15, 1991).

Moran et al., "Human Recombinant Soluble Decay Accelerating Factor Inhibits Complement Activation In Vitro and In Vivo" *Journal of Immunology* 149(5):1736–1743 (Sep. 1, 1992).

Moriuchi et al., "Rat Thy–1 antigen has a hydrophobic segment at the carboxyl terminus" *FEBS Letters* 178(1):105–108 (1985).

Murphy, J.R. et al., "Genetic construction, expression, and melanoma–selective cytotoxicity of a diptheria toxin–related α–melanocyte–stimulating hormone fusion protein" *Proc. Natl. Acad. Sci.* 83:8258–8262 (1986).

Nicholson–Weller et al., "Affected erythrocytes of patients with paroxysmal nocturnal hemoglobinuria are deficient in the complement regulatory protein, decay accelerating factor" *Proc. Natl. Acad. Sci. USA* 80:5066–5070 (Aug. 1983).

Nicholson–Weller et al., "Decay Accelerating Factor (DAF) Peptide Sequences Share Homology with a Consensus Sequence Found in the Superfamily of Structurally Related Complement Proteins and Other Proteins Including Haptoglobin, Factor XIII . . . " *Immunology Letters* 14:307–311 (1987).

Nicholson–Weller et al., "Isolation of a Human Erythrocyte Membrane Glycoprotein with Decay–Accelerating Activity for C3 Convertases of the Complement System" *Journal of Immunology* 129(1):184–189 (Jul. 1982).

Nicholson–Weller et al., "Purification From Guinea Pig Erythrocyte Stroma Of A Decay–Accelerating Factor For the Classical C3 Convertase, C4b,2a" *Journal of Immunology* 127:2035–2039 (1981).

Nicholson–Weller et al., "Surface Membrane Expression by Human Blood Leukocytes and Platelets of Decay–Accelerating Factor, a Regulatory Protein of the Complement System" *Blood* 65(5):1237–1244 (1985).

Nicholson–Weller, A., "Decay Accelerating Factor (CD55)" *Current Topics In Microbiology and Immunology* 178:14 (1992).

Opelz et al., "HL–A and Kidney Transplants: Reexamination" *Transplantation* 17(4):371–382 (1974).

Pangburn et al., "Deficiency of an erythrocyte membrane protein with complement regulatory activity in paroxysmal nocturnal hemoglobinuria" *Proc. Natl. Acad. Sci. USA* 80:5430–5434 (Sep. 1983).

Pangburn et al., "Paroxysmal Nocturnal Hemoglobinuria: Deficiency in Factor H–Like Functions of the Abnormal Erythrocytes" *Journal of Experimental Medicine* 157:1971–1980 (Jun. 1983).

Post et al., "Structure of the Genes for Human Complement Protein Decay Accelerating Factor" *Journal of Immunology* 144(2):740–744 (1990).

Ross et al., "Generation of Three Different Fragments of Bound C3 with Purified Factor I or Serum. I. Requirements for Factor H vs $CR_1$ Cofactor Activity" *Journal of Immunology* 129(5):2051–2060 (Nov. 1982).

Schumacher, M. et al., "Primary structure of Torpedo californica acetylcholinesterase deduced from its cDNA sequence" *Nature* 319:407–409 (1986).

Scopes, R., "Immunoadsorbents" *Protein Purification: Principles and Practice,* Second edition, New York:Springer–Verlag pp. 167–172 (1987).

Seki et al., "A Hydrophobic Transmembrane Segment at the Carboxyl Terminus of Thy–1" *Science* 227:649–651 (Feb. 8, 1985).

Seki, T. et al., "Structural organization of the rat thy–1 gene" *Nature* 313:485–487 (1985).

Smith, M., "In Vitro Mutagenesis" *Ann. Rev. Genet.* 19:423–462 (1985).

Stryer, L., "Amino Acid Sequence Specifies Three–Dimensional Structure" *Biochemistry,* Second edition, W.H. Freeman and Company pp. 32–36 (1981).

Suggs et al., "Use of Synthetic Oligonucleotides as Hybridization Probes: Isolation of Cloned cDNA Sequences for Human $β_2$–Microglobulin" *Proc. Natl. Acad. Sci. USA* 78(11):6613–6617 (Nov. 1981).

Sugita et al., "Improved Method for the Isolation and Preliminary Characterization of Human DAF (Decay–Accelerating Factor)" *Journal of Biochemistry* 100(1):143–150 (1986).

Taylor et al., "Decreased Complement Mediated Binding of Antibody/$^3$H–dsDNA Immune Complexes to the Red Blood Cells of Patients with Systemic Lupus Erythematosus, Rheumatoid Arthritis, and Hematologic Malignancies" *Arthritis and Rheumatism* 26(6):736–744 (Jun. 1983).

Templeton et al., "Construction and Expression of a Recombinant DNA Gene Encoding a Polyomavirus Middle–Size Tumor Antigen with the Carboxyl Terminus of the Vesicular Stomatitis Virus Glycoprotein G" *Molecular & Cellular Biology* 4(2):282–289 (Feb. 1984).

Tse et al., "A Glycophospholipid Tail at the Carboxyl Terminus of the Thy–1 Glycoprotein of Neurons and Thymocytes" *Science* 230:1003–1008 (1985).

Vitetta et al., "Redesigning Nature's Poisons to Create Anti–tumor Reagents" *Science* 238:1098–1104 (1987).

von Heijne, "How Signal Sequences Maintain Cleavage Specificity" *Journal of Molecular Biology* 173:243–251 (1984).

Walters, R., "Affinity Chromatography" *Analytical Chemistry* 57(11):1099A–1114A (Sep. 1985).

Watson, "DNA Sequence of the Herpes Simplex Virus Type 2 Glycoprotein D Gene" *Gene* 26:307–312 (1983).

Weiss et al., "Isolation and characterization of a cDNA encoding a human liver/bone/kidney–type alkaline phosphatase" *Proc. Natl. Acad. Sci. USA* 83:7182–7186 (1986).

Wieben et al., "cDNA Cloning of a Human Autoimmune Nuclear Ribonucleoprotein Antigen" *Proc. Natl. Acad. Sci. USA* 82:7914–7918 (1985).

Wilson, et al., "Mode of Inheritance of Decreased C3b Receptors on Erythrocytes of Patients with Systemic Lupus Erythematosus" *New England J. of Medicine* 307(16):981–986 (Oct. 1982).

Wong et al., "Identification of a Partial cDNA Clone for the Human Receptor for Complement Fragments C3b/C4b" *Proc. Natl. Acad. Sci.* 82:7711–7715 (1985).

Young et al., "Efficient isolation of genes by using antibody probes" *Proc. Natl. Acad. Sci. USA* 80:1194–1198 (Mar. 1983).

FIG. 1A

```
                                                   fnu4HI
                                 fnu4HI            hgaI
                                 bbvI              mspI       thaI
                                 aluI    hinfI     scrFI      hinPI
                                         hinfI     ncil hpaII hhaI
  1  CCGCTGGGCG TAGCTGCGAC TCGGGGGAGT CCCGGCGGCG CGTCCTTGTT
     GGCGACCCGC ATCGACGCTG AGCCCGCTCA GGGCCGCCGC GCAGGAACAA xmaIII              hinPI
           hinPI                              fnu4HI              hhaI
           hhaI                               thaI                fnu4HI
           bssHII                             hinPI         thaI  bbvI
       mspI                                   hhaI          saCII bbvI
       hpaII hinPI                        thaI haeIII bsp1286 haeIII
       scrFI hhaI                         CCGAGCGTGC  CCGGGCGCT
       ncil thaI nlaIII                   GGCTCGCACG  GGCCGCCGA
     CTAACCCGGC GCGCCATGAC CGTCGGCGCG                 roAlaAlaLeu
     GATTGGGCCG CGCGGTACTG GCAGCCGCGC rValAlaArg ProSerValP
                          MetTh                -30 fnu4HI
                            bbvI        fnu4HI
                 aval       mspI        bbvI
                 mnlI       hpaII       scrFI fnu4HI
                 aluI       scrFI       ncil bbvI
 101 GCCCCTTCCTC GGGGAGCTGC CCCGGCTGCT GCTGCTGGTG CTGTTGTGCC
     CGGGGAAGGAG CCCCTCGACG GGGCCGACGA CGACGACCAC GACAACACGG
     ProLeuLeu  GlyGluLeuP  roArgLeuLe  uLeuLeuVal LeuLeuCysLeu
           -20                                     -10 haeIII
          xmaIII
          mspI      haeIII
          hpaII     haeI                        rsaI
          naeI      hphI                        CCCCAGATGT ACCTAATGCC
     TGCCGGCCGT GTGGGTGAC TGTGGCCTTC CCCCAGATGT ACCTAATGCC
     ACGGCCGGCA CACCCACTG ACACCGGAAG GGGGTCTACA TGGATTACGG
     ProAlaVa    lTrpGlyAsp CysGlyLeuP roProAspVa lProAsnAla
                      ↑
                      1                                10
```

FIG. 1B

```
                                                             mnlI
              aluI              rsaI              avaI
             haeIII             aaI           CCGAGGATA    CTGTAATAAC
201 CAGCCAGCTT TGGAAGGCCG TACAAGTTTT  CCGAGGATA    CTGTAATAAC
    GTCGGTCGAA ACCTTCCGGC ATGTTCAAAA  GGGCTCCTAT  GACATTATTG
    GlnProAlaL euGluGlyAr gThrSerPhe ProGluAspT   hrValIleThr
                                       20
                                         scrFI              ddeI
     rsaI       mboII  aluI              bstNI              hinfI
    GTACAAATGT GAAGAAAGCT TTGTGAAAAT  TCCTGGCGAG AAGGACTCAG
    CATGTTTACA CTTCTTTCGA AACACTTTTA  AGGACCGCTC TTCCTGAGTC
    TyrLysCys GluGluSerP heValLysIl   eProGlyGlu LysAspSerVal
            30                                            40
      sau3AI
      dpnI  bglI                                    mboII
301 TGATCTGCCT TAAGGGCAGT CAATGGTCAG ATATTGAAGA    GTTCTGCAAT
    ACTAGACGGA ATTCCCGTCA GTTACCAGTC TATAACTTCT    CAAGACGTTA
    IleCysLe uLysGlySer GlnTrpSerA  spIleGluGl   uPheCysAsn
                    50                                   60
      fnu4HI    nlaIV                    fokI
      bbvI     banI                      sfaNI
      aluI   mnlI bglI
    CGTAGCTGCG AGGTGCCAAC AAGGCTAAAT   TCTGCATCCC TCAAACAGCC
    GCATCGACGC TCCACGGTTG TTCCGATTTA   AGACGTAGGG AGTTTGTCGG
    ArgSerCysG luValProTh rArgLeuAsn   SerAlaSerL euLysGlnPro
                                       70
                 ddeI                   rsaI
401 TTATATCACT CAGAATTATT TTCCAGTCGG   TACTGTTGTG GAATATGAGT
    AATATAGTGA GTCTTAATAA AAGGTCAGCC   ATGACAACAC CTTATACTCA
    TyrIleThr GlnAsnTyrP heProValGl   yThrValVal GluTyrGluCys
                                       80               90
      scrFI
      bstNI           mboII                      hphI
    GCCGTCCAGG TTACAGAAGA GAACCTTCTC   TATCACCAAA ACTAACTTGC
    CGGCAGGTCC AATGTCTTCT CTTGGAAGAG   ATAGTGGTTT TGATTGAACG
    ArgProGl yTyrArgArg GluProSerL   euSerProLy sLeuThrCys
                    100                                 110
      draI                       taqI                    nlaIII
      ahaIII   sau961
      avaII
501 CTTCAGAATT TAAATGGTC  CACAGCAGTC GAATTTTGTA AAAAGAAATC
    GAAGTCTTAA ATTTTACCAG GTGTCGTCAG CTTAAAACAT TTTTCTTTAG
    LeuGlnAsnL euLysTrpSe rThrAlaVal GluPheCysL ysLysLysSer
                    120
```

FIG. 1C

```
                scrFI                              scrFI
                nciI                               bstNI
                mspI                               rsaI
                hpaII
      ATGCCCTAAT CCGGGAGAAA TACGAAATGG TCAGATTGAT GTACCAGGTG
      TACGGGATTA GGCCCTCTTT ATGCTTTACC AGTCTAACTA CATGGTCCAC
      CysProAsn  ProGlyGluI leArgAsnGl yGlnIleAsp ValProGlyGly
                     130                   140 nlaIII                           rsaI
601   GCATATATT  TGGTGCAACC ATCTCCTTCT CATGTAACAC AGGGTACAAA
      CGTATAATAA ACCACGTTGG TAGAGGAAGA GTACATTGTG TCCCATGTTT
      IleLeuPh   eGlyAlaThr IleSerPhes erCysAsnTh rGlyTyrLys
                     150                              160 aluI
                                                  fnu4HI
                 taqI                             bbvI
      TTATTTGGCT CGACTTCTAG TTTTTGTCTT ATTTCAGGCA GCTCTGTCCA
      AATAAACCGA GCTGAAGATC AAAAACAGAA TAAAGTCCGT CGAGACAGGT
      LeuPheGlyS  erThrSerSe rPheCysLeu IleSerGlyS erSerValGln
                     170

701   GTGGAGTGAC CCGTTGCCAG AGTGCAGAGA AATTTATTGT CCAGCACCAC
      CACCTCACTG GGCAACGGTC TCACGTCTCT TTAAATAACA GGTCGTGGTG
      TrpSerAsp  ProLeuProG luCysArgGl uIleTyrCys ProAlaProPro
                     180                              190 hgiAI
                     nsiI                         bsp1286
                     avaII              hphI       nlaIII
      CACAAATTGA CAATGGAATA ATTCAAGGGG AACGTGACCA TTATGGATAT
      GTGTTTAACT GTTACCTTAT TAAGTTCCCC TTGCACTGGT AATACCTATA
      GlnIleAs   pAsnGlyIle IleGlnGlyL euArgAspHi sTyrGlyTyr
                     200                              210 hinfI
                     nlaIII                            sau96I
                                                       haeIII
801   AGACAGTCTG TAACGTATGC ATGTAATAAA GGATTCACCA TGATTGGAGA
      TCTGTCAGAC ATTGCATACG TACATTATTT CCTAAGTGGT ACTAACCTCT
      ArgGlnSerV alThrTyrAl aCysAsnLys GlyPheThrM etIleGlyGlu
                                 220 sau96I
                                                  haeIII
      GCACTCTATT TATTGTACTG TGAATAATGA TGAAGGAGAG TGGAGTGGCC
      CGTAGAGATAA ATAACATGAC ACTTATTACT ACTTCCTCTC ACCTCACCGG
      HisSerIle  TyrCysThrV alAsnAsnAs pGluGlyGlu TrpSerGlyPro
                     230                              240
```

FIG. 1D

```
                                               sau96I
                                               nlaIV
                                               avaII
                                    styI
           bsmI       mnlI          AAATCTCTAA  CTTCCAAGGT  CCCACCAACA
      CACCACCCTGA ATGCAGAGGA                   GAAGGTTCCA  GGGTGGTTGT
 901  GTGGTGGACT  TACGTCTCCT       TTTAGAGATT                          
      ProProGl    uCysArgGly       LysSerLeuT  hrSerLysVa  lProProThr
                       250                                       260
                                                           hphI
      GTTCAGAAAC  CTACCACAGT       AAATGTTCCA  ACTACAGAAG  TCTCACCAAC
      CAAGTCTTTG  GATGGTGTCA       TTTACAAGGT  TGATGTCTTC  AGAGTGGTTG
      ValGlnLysP  roThrThrVa       lAsnValPro  ThrThrGluV  alSerProThr
                                        270 ddeI                                                 CAAGCAACAC
      TTCTCAGAAA  ACCACCACAA       AAACCACCAC  ACCAAATGCT  GTTCGTTGTG
1001  AAGAGTCTTT  TGGTGGTGTT       TTTGGTGGTG  TGGTTTACGA  CAAGCAACAC
      SerGlnLys   ThrThrThrL       ysThrThrTh  rProAsnAla  GlnAlaThrArg
          280                                      290
           rsaI     scrFI                            nlaIII
                    bstNI                                   AACAACCCCA
      GGAGTACACC  TGTTTCCAGG       ACAACCAAGC  ATTTTCATGA  TTGTTGGGGT
      CCTCATGTGG  ACAAAGGTCC       TGTTGGTTCG  TAAAAGTACT  AACAACCCCA
      SerThrPr    oValSerArg       ThrThrLysH  isPheHisGl  uThrThrPro
                       300                                       310
                                                            mRNA Splice Site
           xmnI                                                 bsp1286
           nlaIV                            rsaI            TATCTGGGCA
      AATAAAGGAA  GTGGAACCAC       TTCAGGTACT  ACCCGTCTTC  ATAGACCCGT
1101  TTATTTCCTT  CACCTTGGTG       AAGTCCATGA  TGGGCAGAAG  ATAGACCCGT
      AsnLysGlyS  erGlyThrTh       rSerGlyThr  ThrArgLeuL  euSerGlyHis
                                       320
                                                           nlaIII
                                            mboII           styI
          hincII                             hqaI           ncoI
      CACGTGTTTC  ACGTTGACAG       GTTTGCTTGG  GACGCTAGTA  ACCATGGGCT
      GTGCACAAAG  TGCAACTGTC       CAAACGAACC  CTGCGATCAT  TGGTACCCGA
      ThrCysPhe   ThrLeuThrG       lyLeuLeuGl  yThrLeuVal  ThrMetGlyLeu
          330                                                    340
           ddeI            mboII                             accI
      TGCTGACTTA  GCCAAAGAAG       AGTTAAGAAG  AAAATACACA  CAAGTATACA
1201  ACGACTGAAT  CGGTTTCTTC       TCAATTCTTC  TTTTATGTGT  GTTCATATGT
      LeuThrAM *
                    ddeI
      GACTGTTCCT  AGTTCTTAG        ACTTATCTGC  ATATTGGATA  AAATAAATGC
      CTGACAAGGA  TCAAAGAATC       TGAATAGACG  TATAACCTAT  TTTATTTACG
```

FIG. 1E

```
                 mboII
       hgiAI       sfaNI
       bspl286    fokI
1301 AATTGTGCTC TTCATTTAGG ATGCTTTCAT TGTCTTTAAG ATGTGTTAGG
     TTAACACGAG AAGTAAATCC TACGAAAGTA ACAGAAATTC TACACAATCC hinfI
                                         scrFI         ddeI
       hincII                            bstNI
1401 AATGTCAACA GAGCAAGGAG AAAAAAGGCA GTCCTGGAAT CACATTCTTA
     TTACAGTTGT CTCGTTCCTC TTTTTTCCGT CAGGACCTTA GTGTAAGAAT hinfI
              mnlI
     GCACACCTAC ACCTCTGAA AATAGAACAA CTTGCAGAAT TGAGAGTGAT
     CGTGTGGATG TGGAGAACTT TTATCTTGTT GAACGTCTTA ACTCTCACTA TCCTTTCCTA AAAGTGTAAG AAAGCATAGA GATTTGTTCG TATTTAGAAT
     AGGAAAGGAT TTTCACATTC TTTCGTATCT CTAAACAAGC ATAAATCTTA sau3AI
       sau3AI                                       dpnI
       dpnI  mnlI                                   xhoII
                                                    bglII
1501 GGGATCACGA GGAAAAGAGA AGGAAAGTGA TTTTTTTCCA CAAGATCTGT
     CCCTAGTGCT CCTTTTCTCT TCCTTTCACT AAAAAAAGGT GTTCTAGACA ecoRV
     AATGTTATTT CCACTTATAA AGGAAATAAA AATGAAAAAC ATTATTTGGA
     TTACAATAAA GGTGAATATT TCCTTTATTT TTACTTTTTG TAATAAACCT mtmboII
                                           ddeI
1601 TATCAAAAGC AAATTTTTG CAATTCAGTC TCTTCTAAGC AAAATTGCTA
     ATAGTTTTCG TTTAAAAAC GTTAAGTCAG AGAAGATTCG TTTTAACGAT AAGAGAGATG AACCACATTA TAAAGTAATC TTTGGCTGTA AGGCATTTTC
     TTCTCTCTAC TTGGTGTAAT ATTTCATTAG AAACCGACAT TCCGTAAAAG draI                       nlaIII hphI
       sspI  ahaIII
1701 ATCTTTCCTT CGGGTTGGCA AAATATTTTA AGGTAAACA TGCTGGTGAA
     TAGAAAGGAA GCCCAACCGT TTTATAAAAT TCCATTTGT ACGACCACTT
```

FIG. 1F

```
           scrFI                         hphI           mnlI                              mboII
           bstNI                                                                   hinfI
1701  CCAGGGGTGT TGATGGTGAT ACTACCACTA AAGGGAGGAA TTCCCTCCTT TATAGAATGA AAGACTGAAT
      GGTCCCCACA ACTACCACTA                                 ATATCTTACT TTCTGACTTA
                                                                              mboII
1801  CTTCCTTGTT GCACAAATAG AGTTTGGAAA AGCCTGTGAA AGTGTCTTC
      GAAGGAACAA CGTGTTTATC TCAAACCTTT TCGGACACTT TCCACAGAAG
                draI
                ahaIII                                    sspIsspI
      TTTGACTTAA TGTCTTTAAA AGTATCCAGA GATACTACAA TAGTCAAATA
      ACAGAAATT ACAGAAATT TCATAGGTCT CTATGATGTT ATCAGTTTAT
                                    taqI
                                    hinfI
1901  AGAAAAGATT ATATATTATT TCTGAATCGA GATGTCCATA GTCAAATTTG
      TCTTTTCTAA TATATAATAA AGACTTAGCT CTACAGGTAT CAGTTTAAAC
                            sspI
      TAAATCTTAT TCTTTTGTAA TATTTATTTA TGACAGTGAA
      ATTTAGAATA AGAAAACATT ATAAATAAAT ACTGTCACTT
                                               mboII
                nlaIII                     mboII            mboII
2001  CATTCTGATT TTACATGTAA AACAAGAAAA GTTGAAGAAG ATATGTGAAG
      GTAAGACTAA AATGTACATT TTGTTCTTTT CAACTTCTTC TATACACTTC
                                       sau3AI
                                       dpnI
      AAAAATGTAT TTTTCCTAAA TAGAAATAAA TGATCCCATT TTTTGGTAAA
      TTTTTACATA AAAAGGATTT ATCTTTATTT ACTAGGGTAA AAAACCATTT
2101  AAAAAAAAAA AAAAA
      TTTTTTTTTT TTTTT
```

FIG. 2A

```
                                                  fnu4HI
                                                    mspI        hinPI
                                                    scrFI  hgaI hhaI
                          fnu4HI                    ncilI thaI
                          bbvI                      hpaII hinPI
                    aluI  hinfI         hinfI  hpaII hhaI
  1 CCGCTGGGCG TAGCTGCGAC TCGGGCGAGT AGCCGCCTCA CCCGGCGGCG CGTCCTTGTT
    GGCGACCCGC ATCGACGCTG AGCCCGCTCA TCGGCGGAGT GGGCCGCCGC GCAGGAACAA hinPI
    hhaI
    bssHII                           xmaIII                         hinPI
    mspI                             fnu4HI              thaI fnu4HI  hhaI
    hpaII hinPI                  thaI                    fnu4HI bbvI
    scrFI  hhaI                  hinPI                   sacII bspl286 haeIII
    ncilI  thaI  nlaIII    thaI haeIII      bsp1286      haeII
    CTAACCCGGC GCGCCATGAC CGTCGCGCGG CCGACCGTGC CCGGCGGCT
    GATTGGGCCG CGCGGTACTG GCAGCGCGCC GGCTGGCACG GGCCGCCGA
                          MetTh rValAlaArg ProSerValP roAlaAlaLeu
                                                -30 fnu4HI
                         bbvI
           avaI    fnu4HI mspI                fnu4HI
           mnlI    bbvI   hpaII                bbvI
           mnlI   aluI    scrFI   fnu4HI
                         ncilI   bbvI
 101 GCCCCTCCTC GGGGAGCTGC CCCGGCTGCT GCTGCTGGTG CTGTTGTGCC
     CGGGGAGGAG CCCCTCGACG GGGCCGACGA CGACGACCAC GACAACACGG
     ProLeuLeu GlyGluLeuP roArgLeuLe uLeuLeuVal LeuLeuCysLeu
              -20                                 -10 haeIII
     xmaIII                              haeI
     mspI                   haeI         rsaI
     hpaII         hphI     haeIII
     naeI
     TGCCGGCCGT GTGGGGTGAC TGTGGCCTTC CCCCAGATGT ACCTAATGCC
     ACGGCCGGCA CACCCCACTG ACACCGGAAG GGGGTCTACA TGGATTACGG
     ProAlaVa lTrpGlyAsp CysGlyLeuP roProAspVa lProAsnAla
                         ↑                              10
                         1
```

FIG. 2B

```
                 aluI          rsaI              mnlI
           CAGCCAGCTT  TGGAAGGCCG  TACAAGTTTT  CCCGAGGATA  CTGTAATAAC
           GTCGGTCGAA  ACCTTCCGGC  ATGTTCAAAA  GGGCTCCTAT  GACATTATTG
201        GlnProAlaL  euGluGlyAr  gThrSerPhe  ProGluAspT  hrValIleThr
                          haeIII                             20
                                        hindIII                   ddeI
           rsaI      mboII  aluI                          scrFI     hinfI
           GTACAAATGT  GAAGAAAGCT  TTGTGAAAAT  TCCTGGCGAG  AAGGACTCAG
           CATGTTTACA  CTTCTTTCGA  AACACTTTTA  AGGACCGCTC  TTCCTGAGTC
           TyrLysCys   GluGluSerP  heValLysIl  eProGlyGlu  LysAspSerVal
             30                                 40
           sau3AI
           dpnI bglI                              mboII
           TGATCTGCCT  TAAGGGCAGT  CAATGGTCAG  ATATTGAAGA  GTTCTGCAAT
           ACTAGACGGA  ATTCCCGTCA  GTTACCAGTC  TATAACTTCT  CAAGACGTTA
301        IleCysLe    uLysGlySer  GlnTrpSerA  spIleGluGl  uPheCysAsn
                          50                                  60
           fnu4HI  nlaIV
           bbvI    banI                          fokI            mnlI
           aluI  mnlI bglI                       sfaNI
           CGTAGCTGCG  AGGTGCCAAC  AAGGCTAAAT  TCTGCATCCC  TCAAACAGCC
           GCATCGACGC  TCCACGGTTG  TTCCGATTTA  AGACGTAGGG  AGTTTGTCGG
           ArgSerCysG  luValProTh  rArgLeuAsn  SerAlaSerL  euLysGlnPro
                                      70
                                             rsaI
                  ddeI                                            mnlI
           TTATATCACT  CAGAATTATT  TTCCAGTCGG  TACTGTTGTG  GAATATGAGT
           AATATAGTGA  GTCTTAATAA  AAGGTCAGCC  ATGACAACAC  CTTATACTCA
401        TyrIleThr   GlnAsnTyrP  heProValGl  yThrValVal  GluTyrGluCys
                            80                     90
           scrFI            mboII
           bstNI                                hphI
           GCCGTCCAGG  TTACAGAAGA  GAACCCTTCTC  TATCACCAAA  ACTAACTTGC
           CGGCAGGTCC  AATGTCTTCT  CTTGGAAGAG  ATAGTGGTTT  TGATTGAACG
           ArgProGl    yTyrArgArg  GluProSerL  euSerProLy  sLeuThrCys
                         100                                 110
              sau96I
           draI  avaI               taqI                        nlaIII
           CTTCAGAATT  TAAAATGGTC  CACAGCAGTC  GAATTTTGTA  AAAGAAATC
           GAAGTCTTAA  ATTTTACCAG  GTGTCGTCAG  CTTAAACAT  TTTTCTTTAG
501        LeuGlnAsnL  euLysTrpSe  rThrAlaVal  GluPheCysL  ysLysLysSer
             ahaIII                              120
```

FIG. 2C

```
                        scrFI
                        ncil
                        mspI                                        scrFI
                        hpaII                                       bstNI
                        |                              rsaI         |
     ATGCCCTAAT   TACGGAGAAA   TACGAAATGG   TCAGATTGAT   GTACCAGGTG
     TACGGGATTA   GGCCCTCTTT   ATGCTTTACC   AGTCTAACTA   CATGGTCCAC
     CysProAsn    ProGlyGluI   leArgAsnGl   yGlnIleAsp   ValProGlyGly
                      130                       140
                                nlaIII                             rsaI
     GCATATATT    TGGTGCAACC   ATCTCCCTCT   CATGTAACAC   AGGGTACAAA
601  CGTATATAA    ACCACGTTGG   TAGAGGAGA    GTACATTGTG   TCCCATGTTT
     IleLeuPh     eGlyAlaThr   IleSerPheS   erCysAsnTh   rGlyTyrLys
                      150                                   160
                                                      aluI
                                                      fnu4HI
                                                      bbvI
                taqI
     TTATTTGGCT   CGACTTCTAG   TTTTTGTCTT   ATTTCAGGCA   GCTCTGTCCA
     AATAAACCGA   GCTGAAGATC   AAAAACAGAA   TAAAGTCCGT   CGAGACAGGT
     LeuPheGlyS   erThrSerSe   rPheCysLeu   IleSerGlyS   erSerValGln
                                   170
     GTGGAGTGAC   CCGTTGCCAG   AGTGCAGAGA   AATTATTGT    CCAGCACCAC
701  CACCTCACTG   GGCAACGGTC   TCACGTCTCT   TTAAATAACA   GGTCGTGGTG
     TrpSerAsp    ProLeuProG   luCysArgGl   uIleTyrCys   ProAlaProPro
                      180                       190 nlaIII
                                                          hphI          hgiAI
                                    nsiI                  hinfI  nlaIII bsp1286
     CACAAATTGA   CAATGGAATA   ATTCAAGGGG   AACCGTGACCA   TTATGGATAT
     GTGTTTAACT   GTTACCTTAT   TAAGTTCCCC   TTGCACTGGT   AATACCTATA
     GlnIleAs     pAsnGlyIle   IleGlnGlyG   luArgAspHi   sTyrGlyTyr
                      200                                   210
                                                                     sau961
                                                                     haeIII
     AGACAGTCTG   TAACGTATGC   ATGTAATAAA   GGATTCACCA   TGATTGGAGA   TGGAGTGGCC
801  TCTGTCAGAC   ATTGCATACG   TACATTATTT   CCTAAGTGGT   ACTAACCTCT   ACCTCACCGG
     ArgGlnSer    alThrTyrAl   aCysAsnLys   GlyPheThrM   etIleGlyGlu  TrpSerGlyPro
                      220 rsaI
     GCACTCTATT   TATTGTACTG   TGAATAATGA   ACTTCCTCTC   ACCTCACCGG
     CGTGAGATAA   ATAACATGAC   ACTTATTACT   TGAAGGAGAG   TGGAGTGGCC
     HisSerIle    TyrCysThrV   alAsnAsnAs   pGluGlyGlu   TrpSerGlyPro
                      230                       240
```

FIG. 2D

```
                                   sau96I
                                    nlaIV
                        mnlI        avaII           styI
       bsmI                                                                                     sau96I
901 CACCACCTGA ATGCAGAGGA AAATCTCTAA CTTCCAAGGT CCCACCAACA
    GTGGTGGACT TACGTCTCCT TTTAGAGATT GAAGGTTCCA GGGTGGTTGT
    ProProGl uCysArgGly LysSerLeuT hrSerLysVa lProProThr
                 250                                    260
                                                                       hphI
    GTTCAGAAAC CTACCACAGT AAATGTTCCA ACTACAGAAG TCTCACCAAC
    CAAGTCTTTG GATGGTGTCA TTTACAAGGT TGATGTCTTC AGAGTGGTTG
    ValGlnLysP roThrThrVa lAsnValPro ThrThrGluV alSerProThr
                                  270
       ddeI
1001 TTTCAGAAAA ACCACCACAA ACCAAATGCT CAAGCAACAC
     AAGTCTTTTT TGGTGGTGTT TGGTTTACGA GTTCGTGTG
     SerGlnLys ThrThrThrTh rProAsnAla GlnAlaThrArg
              280                               290
                scrFI
        rsaI    bstNI                                nlaIII
     GGAGTACACC TGTTTCCAGG ACAACCAAGC ATTTTCATGA AACAACCCCA
     CCTCATGTGG ACAAAGGTCC TGTTGGTTCG TAAAAGTACT TTGTTGGGGT
     SerThrPr  oValSerArg ThrThrLysH isPheHisGl uThrThrPro
                      300                            310
        xmnI
        nlaIV                         rsaI     mboII
1101 AATAAAGGAA GTGGAACCAC TTCAGGTACT ACCCGTCTTC TATCTGTTC
     TTATTTCCTT CACCTTGGTG AAGTCCATGA TGGCAGAAG ATAGACAAG
     AsnLysGlyS erGlyThrTh rSerGlyThr ThrArgLeuL euSerGlySer
                                         320
               scrFI                  sau3AI
        hphI    bstNI                  dpnI         aluI  pstI
     TCGTCCTGTC ACCCAGGCTG GTGTGATCGT AGCTCACTGC
     AGCAGGACAG TGGGTCCGAC CACACTAGCA TCGAGTGACG
     ArgProVal ThrGlnAlaG lyMetArgTr pCysAspArg SerSerLeuGln
               330                      340
                 scrFI                                           bstXI
        taqI     bstNI                             mnlI
1201 AGTCTCGAAC TCCTGGGTTC AAGCGATCCT TCCACTTCAG CCTCCCAAGT
     TCAGAGCTTG AGGACCCAAG TTCGCTAGGA AGGTGAAGTC GGAGGGTTCA
     SerArgTh  rProGlyPhe LysArgSerP heHisPheSe rLeuProSer
                  350                                  360
        aluI rsaI    bsp1286                   hincII                hgaI
     AGCTGGTACT ACAGGCACA CGTGTTTCAC GTTGACAGGT TTGCTTGGGA
     TCGACCATGA TGTCCGTGT GCACAAAGTG CAACTGTCCA AACGAACCCT
     SerTrpTyrT yrArgAlaHi sValPheHis ValAspArgP heAlaTrpAsp
                                           370
```

FIG. 2E

```
                   nlaIII                      ddeI          mboII            mboII
            styI
            ncoI
1301 CGCTAGTAAC CATGGGCTTG CTGACTTAGC CAAAGAAGAG TTAAGAAGAA
     GCGATCATTG GTACCCGAAC GACTGAATCG GTTTCTTCTC AATTCTTCTT
     AlaSerAsn HisGlyLeuAl aAspLeuAl aLysGluGlu LeuArgArgLys
     380                                       390
                accI                           ddeI
     AATACACACA AGTATACAGA CTGTTCCTAG TTTCTTAGAC TTATCTGCAT
     TTATGTGTGT TCATATGTCT GACAAGGATC AAAGAATCTG AATAGACGTA
     TyrThrGln ValTyrArg nValPheLeuV LeuPheLeuV alSerAM*
                                       400
                                       mboII
                             hgiAI           sfaNI
                             bsp1286         fokI
1401 ATTGGATAAA ATAAATGCAA TTGTGCTCTT CATTTAGGAT GCTTTCATTG
     TAACCTATTT TATTTACGTT AACACGAGAA GTAAATCCTA CGAAAGTAAC
                             hincII
     TCTTTAAGAT GTGTTAGGAA TGTCAACAGA GCAAGGAGAA AAAAGGCAGT
     AGAAATTCTA CACAATCCTT ACAGTTGTCT CGTTCCTCTT TTTTCCGTCA
         hinfI                       mnlI
      scrFI         ddeI
      bstNI
1501 CCTGGAATCA CATTCCTTAGC CTCCTTGAAAA TAGAACAACT
     GGACCTTAGT GTAAGAATCG GAGAACTTTT ATCTTGTTGA
              hinfI
     TGCAGAATTG AGAGTGATTC CTTTCCTAAA AGTGTAAGAA AGCATAGAGA
     ACGTCTTAAC TCTCACTAAG GAAAGGATTT TCACATTCTT TCGTATCTCT
         sau3AI
         dpnI    mnlI
1601 TTTGTTCGTA TTTAGAATGG GATCACGAGG AAAAGAGAAG GAAAGTGATT
     AAACAAGCAT AAATCTTACC CTAGTGCTCC TTTTCTCTTC CTTTCACTAA
```

FIG. 2F

```
              sau3AI
              dpnI
              xhoII
              bglII
     TTTTTCCACA AGATCTGTAA TGTTATTTCC ACTTATAAAG GAAATAAAAA
     AAAAAGGTGT TCTAGACATT ACAATAAAGG TGAATATTTC CTTTATTTTT ecoRV                                      mboII
1701 TGAAAAACAT TATTTGGATA TCAAAAGCAA ATAAAACCCA ATTCAGTCTC
     ACTTTTTGTA ATAAACCTAT AGTTTTCGTT TATTTTGGGT TAAGTCAGAG ddeI
     TTCTAAGCAA AATTGCTAAA GAGAGATGAA CCACATTATA AAGTAATCTT
     AAGATTCGTT TTAACGATTT CTCTCTACTT GGTGTAATAT TTCATTAGAA draI
                                                    ahaIII
                                               sspI ATATTTTAAA
1801 TGGCTGTAAG GCATTTTCAT CTTTCCTTCG GGTTGGCAAA TATAAAATTT
     ACCGACATTC CGTAAAAGTA GAAAGGAAGC CCAACCGTTT nlaIII hphI  scrFI                hphI          mnlI
            bstNI               AGGGGTGTTG ATGGTGATAA GGGAGGAATA
     GGTAAACATG CTGGTGAACC                 TACCACTATT CCCTCCTTAT
     CCATTTGTAC GACCACTTGG TCCCCACAAC
                     hinfI
              mboII                                 TTTGGAAAAG
1901 TAGAATGAAA GACTGAATCT TCCTTGTGTGC ACAAATAGAG AAACCTTTTC
     ATCTTACTTT CTGACTTAGA AGGAACAACG TGTTTATCTC mboII                                         taqI
                                                        hinfI
                                       ATATTATTTC TGAATCCAGA
     CCTCTGAAAG GTGTCTTCTT TGACTTAAATG TTTTCTAATA TATAATAAAG ACTTAGGTCT
     GGACACTTTC CACAGAAGAA ACTGAATTAC                  AGAAATTTTC ATAGGTCTCT
                                              draI
        sspIpI                               ahaIII
2001 TACTACAATA TTAACATAAG AAAAGATTAT TCTTTAAAAG TATCCAGAGA
     ATGATGTTAT AATTGTATTC TTTTCTAATA AGAAATTTTC sspI
                                                   TTTATTTATA
     TGTCCATAGT CAAATTTGTA AATCTTATTC TTTTGTAATA AAATAAATAT
     ACAGGTATCA GTTTAAACAT TTAGAATAAG AAAACATTAT nlaIII
2101 TTTATTTATG ACAGTGAACA TTCTGATTTT ACATGTAAAA CAAGAAAAGT
     AAATAAATAC TGTCACTTGT AAGACTAAAA TGTACATTTT GTTCTTTTCA
```

FIG. 2G

```
         mboIII
     mboII      mboII
     TGAAGAAGAT ATGTGAAGAA AAATGTATTT TTCCTAAATA           sau3AI
     ACTTCTTCTA TACACTTCTT TTTACATAAA AAGGATTTAT           dpnI
                                                 GAAATAAATG
                                                 CTTTATTTAC
     sau3AI
     dpnI
2201 ATCCCATTTT TTGGTAAAAA AAAAAAAAAA AAA
     TAGGGTAAAA AACCATTTTT TTTTTTTTTT TTT
```

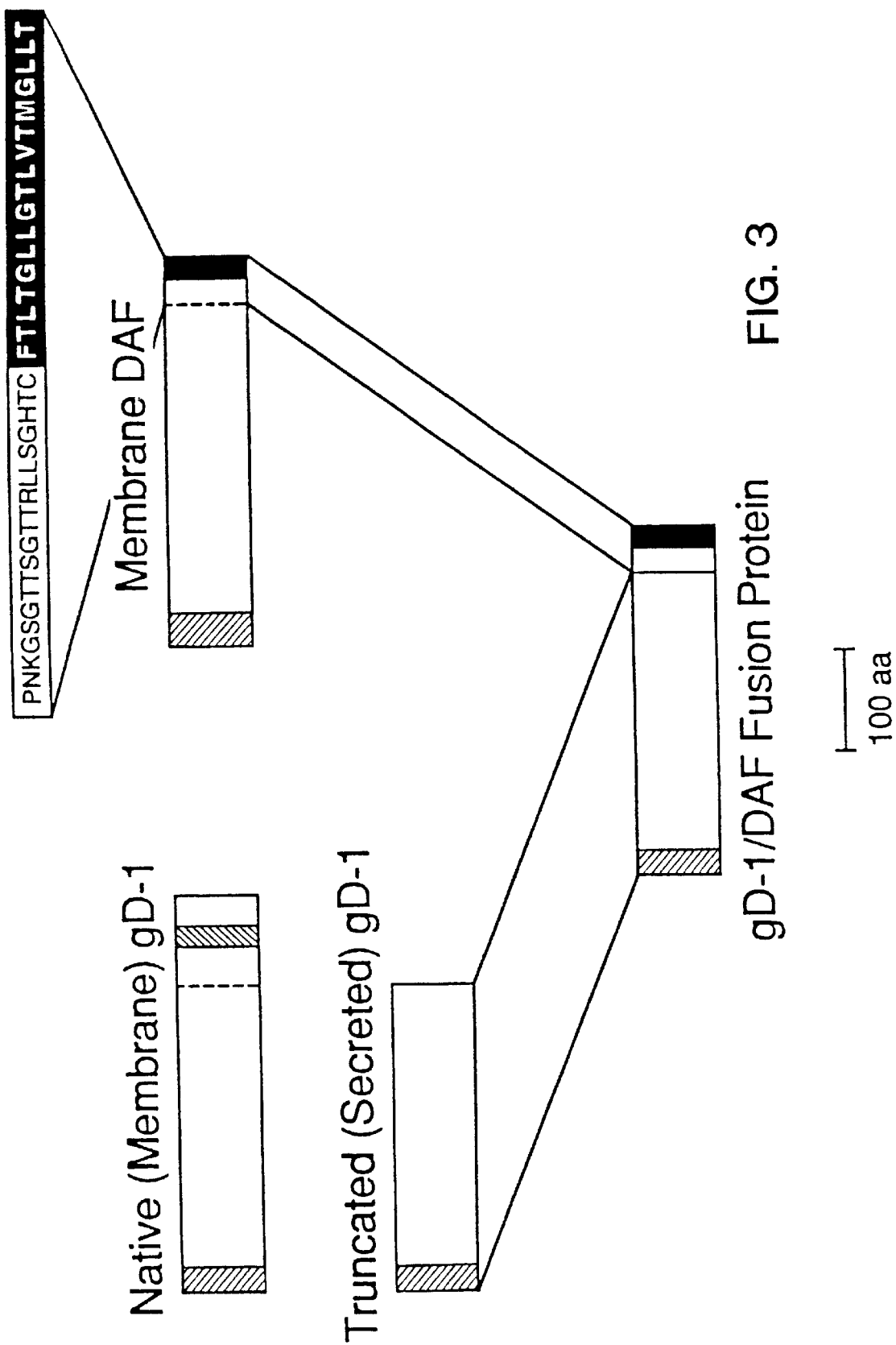

DECAY ACCELERATING FACTOR (DAF) AND NUCLEIC ACID ENCODING IT

This application is a continuation of copending U.S. application Ser. No. 08/358,283 filed Dec. 19, 1994(U.S. Pat. No. 5,763,224) which is a continuation of U.S. application Ser. No. 08/017,934 filed Feb. 12, 1993 (U.S. Pat. No. 5,374,548), which application is a continuation-in-part of U.S. application Ser. No. 07/811,048 filed Dec. 19, 1991 (U.S. Pat. No. 5,264,357), which application is a divisional of U.S. application Ser. No. 07/083,757 filed Aug. 6, 1987 (U.S. Pat. No. 5,109,113), which application is a continuation-in-part of U.S. application Ser. No. 06/859,107 filed May 2, 1986 (Abandoned), to which applications priority is claimed under 35 USC § 120.

This application relates to the preparation of decay is accelerating factor (hereinafter abbreviated as DAF) in recombinant cell culture. In particular, it is concerned with the large scale manufacture of DAF suitable for pharmaceutical or diagnostic use.

Antigenic cells targeted by the humoral immune response are lysed by a process called complement activation. This process consists of a series or cascade of proteolytic activities initiated by the binding of antibody with its antigen. The components that participate in complement activation are many and complex, although for the purposes herein the most important are C4b and C3b. In a key step in complement activation, these two proteins become covalently associated with the target cell surface and then serve as anchors for the assembly of C3 and C5 convertases, the amplifying enzymes of the cascade.

Complement activation must focus only on the target and must not occur on host cells. However, in the course of complement activation, large numbers of nascent C4b and C3b fragments are liberated into the fluid phase. Most react with water, but some by chance could bind to nearby host cells and lead to their damage. For this and possibly other reasons, the activities of bound, as well as free, C3b and C4b fragments are under strict control by a complex system of serum and membrane proteins.

Recent evidence (Medof. et al. 1982. "J. Exp. Med." 156:1739; Medof, et al., 1984. "J. Exp. Med." 159:1669) suggests that regulation of the activities of membrane-bound C4b and C3b is distinct from control of the fluid phase fragments. The functions of the former are controlled mainly by two membrane proteins: the C3b/C4b receptor (CR1) and DAF. CR1 dissociates C2 and factor B from C4b and C3b in C3 and C5 convertase complexes and promotes the cleavage of C3b (Medof, et al., *J. Exp. Med.* 156:1739 [1982]; Fearon, D. T. *Proc. Natl. Acad. Sci. USA:*76:5867 [1979]; Medicus, et al., *Eur. J. Immunol.* 13:465 [1983]; and Ross, et al., *J. Immunol.* 129:2051 [1982]) and C4b (Medof, et al., *J. Exp. Med.* 159:1669 [1984]; Iida et al., *J. Exp.Med.* 153:1138 [1981]) by the serum enzyme C3b/C4b inactivator (I). DAF has been shown also to enhance the decay dissociation of C2 and factor B from C3 convertases (Nicholson-Weller et al., *J. Immunol.* 129:205 [1982] and Pangburn, M. K. et al., *J. Exp. Med.* 157:1971 [1983]). The reason for the apparent redundancy in regulatory activities of the two membrane factors and their respective roles in convertase control has remained unclear. Abnormalities of CR1have been found in systemic lupus erythematosus (SLE) (Miyakawa, Y. et al., *Lancet* 2:493 [1981]; Iida, K. et al., *J. Exp. Med.* 155:1427 [1982]; Wilson, J. G. et al., *N. Engl. J. Med.* 307:981 [1982]; Taylor, R. P. et al., *Arthritis Rheum.* 26:736 [1983]), a condition associated with defective immune complex handling, and abnormalities of DAF have been found in paroxysmal nocturnal hemoglobinuria (PNH) (Pangburn, M. K. et al., *J. Exp. Med.* 157:1971 [1983]; Pangburn, J. K. et al., *Proc. Natl. Acad. Sci.* 80:5430 [1983]; Nicholson-Weller, A. et al., *Proc. Natl. Acad. Sci.* 80:5066 [1983]), a condition associated with heightened susceptibility of blood cells to lysis.

DAF was reported to have been purified as a single 70 Kd band on silver stained SDS-PAGE from a pooled extract of human erythrocyte stroma (Medof et al., *J. Exp. Med.* 160:1558 [1983]). The molecule was hydrophobic and tended to form multimers of greater than or equal to 150 Kd as determined by molecular sieve chromatography. Purified DAF could reassociate with red blood cells. Only a small number of DAF molecules (less than 100) had a significant effect on the hemolytic effect of activated complement. Medof et al. concluded that DAF can only function intrinsically within the cell membrane, and suggested that it offered the possibility of correcting in vitro the defect in the membranes of cells from patients with PNH.

Existing methods for obtaining DAF are unsatisfactory for its commercial preparation. Red cells contain extremely small quantities of DAF. Furthermore, blood contains viruses and other biologically active components which pose a risk of adverse reactions in recipients or users.

Red blood cell DAF is limited to the native membrane bound form, including any naturally occurring alleles as may exist. Methods are needed for synthesizing amino acid and glycosylation variants which can function as DAF agonists or antagonists, or which will exhibit other desirable characteristics such as the absence of C-terminal lipid, resistance to proteases, or the ability to deliver DAF to the membranes of target cells.

Accordingly, it is an object herein to prepare DAF in commercial quantity from a therapeutically acceptable source.

It is a further object of obtain human DAF from a source that is completely uncontaminated with other human proteins.

It is an additional object to prepare amino acid sequence and glycosylation variants of DAF.

Other objects of this invention will be apparent from the specification as a whole.

SUMMARY

The objects of this invention are accomplished by expression of DAF in recombinant cell culture, a process that fundamentally comprises providing nucleic acid encoding DAP, transforming a host cell with the DAF-encoding nucleic acid, and culturing the cell in order to express DAF in the host cell culture.

The method of this invention enables the preparation of novel forms of DAF, including amino acid sequence variants and glycosylation variants. Amino acid sequence variants consist of deletions, substitutions and insertions of one or more DAF amino acid residues. DAF also is expressed in a form unaccompanied by the glycosylation associated with the native DAF (including unaccompanied by any glycosylation whatsoever), obtained as a product of expression of DAF in heterologous recombinant cell culture. DAF in any form as a component of a recombinant cell culture is novel.

Unexpectedly, I discovered during my studies of cell processing of DAF mRNA that the membrane-bound form of DAF (mDAF) is not the only form in which it is expressed in vivo. In fact, another form of DAF exists, called sDAF. This form is encoded by an mRNA species from which the last 3' intron has not been spliced, resulting in an amino acid sequence C-terminal to residue 327 that is entirely different from that of MDAF. The novel C-terminus of sDAF is postulated to result in vivo in the secretion of the protein into the blood stream (where it may be biologically active) because the presence of the intron changes the reading frame of the last exon so as to eliminate the "signal" directing attachment of phosphatidylinositol (the membrane anchor for mDAF). This novel form of DAF was unappreciated until the pioneering work herein was accomplished, and it differs from MDAF in containing an antigenically distinct C-terminus. ODAF is useful in diagnosis of PNH since it is now possible to determine whether the condition in an individual results from a failure to express any of the DAF gene or a failure of post-translational processing to attach the phosphatidylinositol anchor.

Novel nucleic acids also are provided, including (1) cell free nucleic acid identified as encoding DAF, including genomic DNA, cDNA or RNA, (2) DNA encoding DAP free of an untranslated intervening sequence (introns) or flanking genomic DNA, and (3) nucleic acid encoding DAF which is free of nucleic acid encoding any other protein homologous to the source of the nucleic acid that encodes DAF. Also within the scope of this invention is nucleic acid which does not encode DAF but which is capable of hybridizing with nucleic acid encoding DAF.

Nucleic acid encoding DAF is useful in the expression of DAF in recombinant cell culture or for assaying test samples for the presence of DAF-encoding nucleic acid. Labelled DAF-encoding or hybridizing nucleic acid is provided for use in such assays.

Recombinant DAF is formulated into therapeutically acceptable vehicles and administered for the treatment of PNH or inflammatory or cell lytic autoimmune diseases. DAF conjugates or fusions are prepared that deliver DAF to target cells in order to inhibit complement activation at the surfaces of such cells.

The conjugates or fusions are useful for ameliorating allograft rejection or autoimmune diseases.

The carboxyl terminal domain that specifies glycophospholipid membrane anchor attachment for MDAF (referred to as the GPI signal domain; wherein GPI is an abbreviation of glycophosphatidylinositol), or functionally equivalent domains from other proteins which also are anchored by glycophospholipids, are fused to proteins or multimers of such proteins which are heterologous to the source of the GPI signal domain, for example hormones, antigens (especially from infectious organisms), allergens, immunoglobulins, enzymes, receptors and the like. The anchor fusions are used in combination with the recombinant cells which express them or are recovered and formulated into therapeutic compositions, used as diagnostic assay components, or employed in affinity purification procedures. The fusions will contain the heterologous polypeptide fused at its C-terminus to the GPI signal domain, that specifies a processing event in the cell that results in cleavage and removal of the GPI signal domain, and covalent attachment of a GPI anchor to the new C-terminus of the protein. Thus, the last about 30–50 residues of DAF contain a signal (the "GPI signal") that directs a processing event in cells in which the last about 28 residues are proteolytically removed and replaced with a hydrophobic glycolipid (GPI) that acts as a membrane anchor.

Another aspect of the invention is a method for targeting a liposome to a cell of interest, comprising incorporating into the liposome a GPI-linked protein produced by fusing a GPI signal domain to a polypeptide heterologous to the GPI signal domain.

Another aspect of the invention is a composition comprising a liposome, wherein a GPI-linked polypeptide is incorporated into the liposome.

BRIEF DESCRIPTION OF THE DRAWINGS

FIGS. 1a–1f depict the cDNA sequence for clones λ33 (to the HindIII site at residue 1) and λ47 (HindIII to the 3' end) (SEQ ID NO:1). The point at which the intron is removed is designated by an asterisk. The probable phosphatidylinositol derivation site is $Cys_{330}$ and the C-terminal hydrophobic region extends from residues 331–347. Amino acid residues are numbered from the mature amino acid terminus at $Asp^1$ (SEQ ID NO: 2).

FIGS. 2a–2g depict the cDNA sequence of clones λ33 (to the HindIII site at residue +1) and λ41 (HindIII to 3' end) (SEQ ID NO:3) encoding human sDAF. The unspliced intron in the cDNA encoding sDAF is bracketed. Restriction enzyme sites are shown using conventional abbreviations. The predicted amino acid sequence (SEQ ID NO: 4) for each DAF predicted species is shown, together with the secretory leader and mature N-terminus of each (designated by arrows).

FIG. 3 is a schematic diagram showing the regions of HSV 1 glycoprotein D (gD-1) and DAF that are present in the gD-1/DAF fusion protein produced in Example 3. Truncated (secreted) gD-1 was constructed from native (membrane) gD-1 (14) and comprises amino acids 1–300, including the hydrophobic signal sequence (residues 1–25, indicated as a grey area). The hydrophobic membrane spanning domain (residues 340–360, cross-hatched region) and the C-terminal hydrophobic domain (residues 361–393) are excluded. The point of truncation (residue 300) is indicated by a broken line. Truncated gD-1 was fused to residue 311 of membrane DAF. The gD-1/DAF fusion contains the last 37 residues of membrane DAF predicted from the cDNA sequence (residues 311–347) that comprises the GPI signal domain, which includes a C-terminal hydrophobic region (residues 331–347, depicted in black). A similar fusion, gp120/DAF, was constructed in which gD-1 was replaced with HIV-1 IIIB gp120. Expression of this fusion in 293 cells produced GPI-linked gp120.

DETAILED DESCRIPTION OF THE INVENTION

Figure 4:
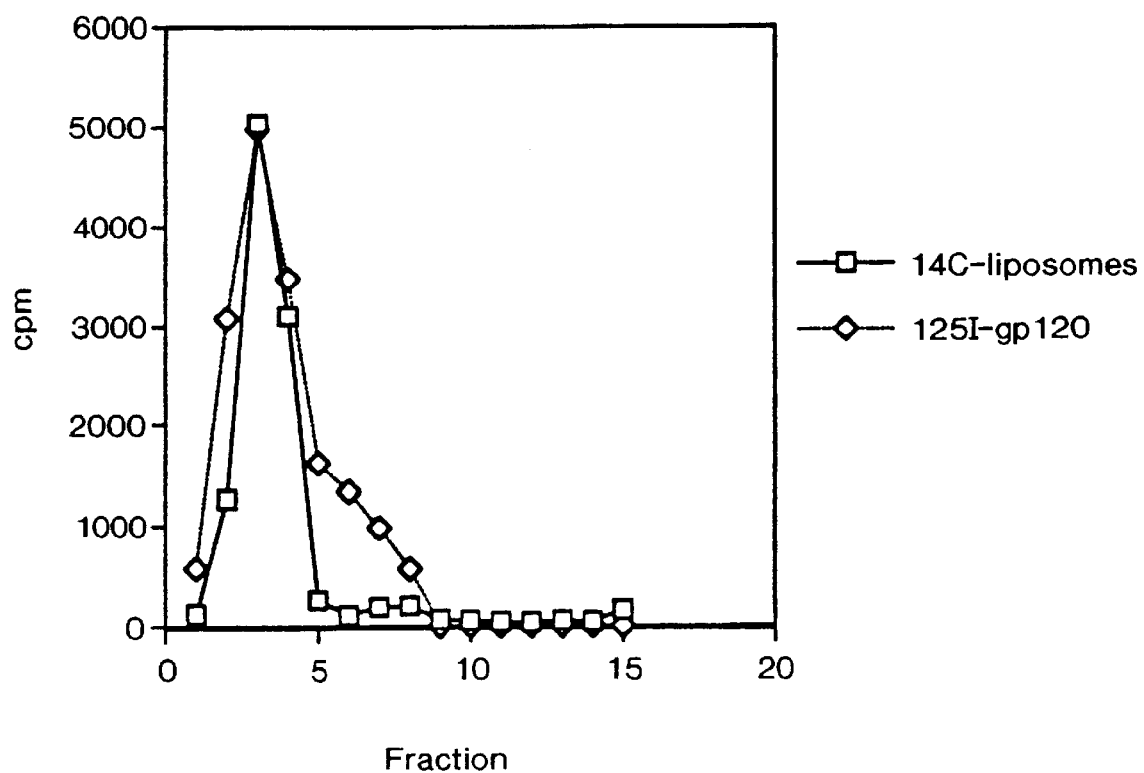
FIG. 4. is a graph depicting sucrose gradient fractionation of gp120/DAF/liposomes. "gp120/DAF" refers to GPI-linked gp120, produced by expression of the fusion of the DAF GPI signal domain to the cDNA encoding gp120. $^{125}$I-labeled gp120/DAF (3.5µg, in 0.8% octyl glucoside) was mixed with $^{14}$C-labeled liposomes (3 mg/ml of lipid, composed of equimolar amounts of phosphatidylcholine and cholesterol) in 685µl of phosphate buffered saline (PBS). The mixture was dialyzed overnight and 200µl was loaded on a 3–25% sucrose gradient and centrifuged at 250,000 xg for 4.5 h at 4° C. Sequential fractions were collected from the top of the gradient and counted to determine the position of the $^{125}$I-labeled gp120/DAF. A parallel gradient containing $^{14}$C-labeled liposomes alone was analyzed to determine the position of the liposomes.

DAF is defined to be any molecule having the precursor or mature amino acid sequence set forth in FIGS. 1 or 2 as well as their amino acid sequence or glycosylation variants (including natural alleles) which are capable of exhibiting a biological activity in common with the native DAF of FIGS. 1 or 2. Henceforth, the term DAF shall mean either or both forms unless otherwise appropriate. Native DAF is DAF obtained from serum, blood cells or other animal fluids or tissues. DAF biological activity is defined as any of 1) immological cross-reactivity with at least one epitope of native DAF, or 2) the possession of at least one hormonal, regulatory or effector function qualitatively in common with native DAF. Since amino acid sequence variations of DAF having antagonist or agonist activity are included, an amino acid sequence variant need not exhibit any DAF immunomodulatory activity to fall within the definition of DAF. For example, a variant may act as an antagonist and competitively inhibit native DAP, yet have no immunomodulatory activity per se. Alternatively, the variant may be neither an antagonist nor have immunomodulatory activity, but still fall within the definition if it remains capable of cross-reacting with antibody raised against native DAF. An example of a presently known DAF immunomodulatory activity is inhibition of C4b2a functional activity (Medof et al., 1984, Id.).

Amino acid sequence variants of DAF include deletions from, or insertions or substitutions of residues within the pre or mature DAF sequence shown in FIGS. 1 or 2. Amino acid sequence deletions generally range from about 1 to 10 residues and typically are contiguous. Contiguous deletions ordinarily are made in even numbers of residues, but single or odd numbers of deletions are within the scope hereof. Representative deletions are [des $Cys_{330}$] mature mDAF, [des $Cys_{330}$–$Thr_{347}$] mature mDAF, [des Thr2 –$Gly_{327}$] mature sDAP. A particularly interesting deletion is $Cys_{330}$–$Thr_{347}$ from mDAF. This eliminates the membrane anchor attachment site and the GPI signal domain, resulting in a molecule that, like sDAF, is secreted but which bears none of the is unique antigenic determinants of sDAP.

Insertions also are preferably made in even numbers of residues when the variation falls within the mature DAF sequence, although insertions may range from 1 to 5 residues in general. However, insertions also include fusions onto the amino or carboxyl termini of DAF or from 1 residue to polypeptides of essentially unrestricted length. An example of a single terminal insertion is mature DAF having an N-terminal methionyl. This variant is an artifact of the direct expression of DAF in recombinant cell culture, i.e., expression without a signal sequence to direct the secretion or cell membrane association of mature DAF. Other examples of terminal insertions include 1) fusions of heterologous signal sequences to the N-terminus of mature DAF in order to facilitate the secretion of mature DAF from recombinant hosts, 2) fusions of immunogenic polypeptides, e.g. bacterial polypeptides such as beta-lactamase or an enzyme encoded by the *E. coli* trp locus and 3) fusions with cell surface binding substances, including hormones, growth factors or antibodies. Fusions with cell surface binding substances need not be produced by recombinant methods, but can be the product of covalent or noncovalent association with DAF, including its phosphatidylinositol group. For example, an antibody or fragment thereof bearing the variable region is covalently bound to, or expressed in recombinant cell culture as a fusion with, the C-terminus of DAF. For amelioration of allograft rejection the DAF is bound to antibodies specific for the HLA antigens of the allograft. The antibody and DAF are covalently bounded, for example, by the method of EP 170,697A, although other methods for linking proteins are conventional and known to the artisan. Immunogenic fusions are useful for preparing immunogenic DAFs suitable as vaccines for preparing anti-DAF antibodies. These are useful for the preparation of diagnostic reagents. Representative insertions are [$Thr_{329}LeuLeuCys_{330}$] mature DAF, [$Arg_{100}HisArg_{101}$] mature DAF, [$Lys_{125}GlnLys_{126}GlnLys_{127}$] mature DAF, [$Pro_{193}LeuLeuAla_{194}$] mature DAF, [$Pro_{247}AspAspGlu_{248}$] mature DAF, [$Thr_{282}SerSerThr_{283}$] mature DAF, and [$Gly_{316}ThrThrThr_{317}$] mature DAF.

The third group of variants are those in which at least one residue in the DAF molecule has been removed and a different residue inserted in its place. Such substitutions generally are made in accordance with following Table.

TABLE 1

| Original Residue | Exemplary Subutitutions |
| --- | --- |
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg, gln; glu |
| Met | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet of helical conformation, (b) the charge or hydrophobicity of the molecule at the target site or (c) the bulk of the side chain. The substitutions in general expected to produce the greatest changes in DAP properties will be those in which (a) a hydrophilic residue, e.g. seryl or threonyl, is substituted for (or by) a hydrophobic residue, e.g. leucyl, isoleucyl, phenylalanyl, valyl, or alanyl; (b) a cysteine or proline is substituted for (or by) any other residue; (c) a residue having an electropositive side chain, e.g., lysyl, arginyl, or histidyl, is substituted for (or by) an electronegative residue, e.g.; glutamyl or aspartyl; or (d) a residue having a bulky side chain, e.g., phenylalanine, is substituted for (or by) one not having such a side chain, e.g. glycine.

Representative substituted DAFs are $[Cys_{330} \rightarrow Met]$ mature mDAF, $[Cys_{330} \rightarrow Ser]$ mature mDAF, $[Cys_2 \rightarrow Ser]$ mature mDAF, $[Lys_{125}Lys_{126} \rightarrow Gln]$ mature DAF, $[Gly_{144} \rightarrow Pro]$ mature DAF, $[Ile_{146} \rightarrow Met]$ mature DAF, $[Phe_{169} \rightarrow Tyr]$ mature DAF, $[Pro_{192} \rightarrow Gly]$ mature DAF, $[Ile_{201} \rightarrow Leu]$ mature DAF, $[Asn_{236}Asn_{237} \rightarrow AspAsp]$ mature DAF, $[Glu_{239} \rightarrow Asp]$ mature DAF, $[Ser_{256} \rightarrow Tyr]$ mature DAF, $[Val_{268} \rightarrow Phe]$ mature DAF, $[Lys_{285} \rightarrow Gln]$ mature DAF, $[Thr_{294} \rightarrow Ser]$ mature DAF and $(Leu_{324} \rightarrow Ser]$ mature DAF.

The above described variants are made in either sDAF or mDAF. The following variants are made in the unique sDAF C-terminal: $[Lys_{352} \rightarrow Gln]$ mature sDAF, $[Cys_{339} \rightarrow Ser]$ mature sDAF, $[Arg_{394} \rightarrow His]$ mature sDAF and mature sDAF $[Leu_{403} Phe_{404} Leu_{405} \rightarrow SerTyrser]$ mature sDAF.

For the purposes herein, any naturally occurring alleles are not included within the scope of DAF variants because the variants described herein are predetermined DAF variants.

The C-terminal domain of MDAF contains a signal (referred to as the "GPI signal domain") which directs attachment of a GPI membrane anchor in the course of post-translational processing. This domain contains about from 29–37 residues and is removed prior to attachment of the GPI anchor to the C-terminal residue carboxyl. This domain or any fragment of mDAF containing it, is produced as a fusion with any other polypeptide for which it is desired to create a membrane-bound form. It will be understood that "GPI-linked" when used in reference to expressed fusions refers to the post-translationally modified fusion, as will be described more fully infra. For example, an ordinarily secreted hormone is produced in recombinant cell culture as a C-terminal fusion of the preprotein with the GPI signal domain of mDAF. Rather than being secreted this fusion will become GPI-linked during processing and will be transported to the cell membrane and remain lodged there by virtue of the GPI anchor. Such recombinant cells are useful as immunogens or vaccines for the hormone or other selected polypeptide. Sequestering the polypeptide in the membrane also protects it from dilution into the culture medium. Finally, fusion polypeptides having C-terminal lipids are useful in diagnostic assays for the polypeptides or their antibodies since the terminal lipid provides a convenient site for adsorption onto microtiter or test tube surfaces and the like.

Other proteins are known that contain C-terminal domains substituted with phospholipid anchors. Such proteins include Thy-1 (Low et al., *Nature* (London) 318:62 [1985] and Tse et al., *Science* 230:1003 [1985]), the variant surface glycoproteins (VSGs).of African trypanosomes (Ferguson et al., *J. Biol. Chem.* 260:14547 [1985]), acetylcholinesterase (Futerman et al., *Biochem. J.* 226:369 [1985]), 5' nucleotidase (Low et al., *Biochim. Biophys. Acta* 508:565 [1978]) as well as DAF (Davitz et al., *J. Exp. Med.* 163:1150 [1986] and, Medof et al., *Biochemistry* 25:6740 [1986]). Attachment of the DAF anchor, which contains glycosylated phosphatidylinositol (PI) and ethanolamine, apparently occurs following proteolytic removal of 17–31 C-terminal residues from mDAF (Low, M. G. *Biochem J.*, 244:1–13 [1987] and Cross, G. A. M., *Cell* 48:179–181 [1987]).

In order to construct fusions of a desired polypeptide and a GPI signal domain, DNA encoding the C-terminal about 30–50 residues of a polypeptide ordinarily bearing such an anchor is ligated to DNA encoding the desired polypeptide, or to a suitable fragment multimer or amino acid sequence variant thereof. The DNA encoding the GPI signal is inserted at the C-terminus of the desired protein. The GPI signal includes a cleavage attachment site for the anchor as well as a short, approximately 10–20 residue, hydrophobic sequence located C-terminal to the cleavage site. This is accomplished by routine procedures well known to those skilled in the art. For example, the DNA encoding the selected GPI signal is synthesized by in vitro methods or by obtaining a suitable fragment from CDNA or genomic DNA encoding the native anchored protein. Since the anchor domain is found within about the COOH-terminal about 30 to 50 residues encoded by the CDNA one should use DNA encoding approximately the COOH— terminal about 30 to 50 residues.

Many proteins in addition to DAF are known to contain glycophospholipid anchors, and their amino acid sequences (including the C-terminal about 20–50 residues which will be employed as GPI signal domains in heterologous fusions) are known. Examples include acetylcholinesterase (M. Schumacher et al., *Nature* 319:407–409 [1986]), Thy-1 (T. Seki et al., *Nature* 313:485–487 [1985] and T. Moriuchi et al. FEBS Lett. 178:105–108 [1985]), VSG (T. Brucei) (Cross, Philos. Trans. R. Soc. London, Ser. B 307:3–12 [1984]) and alkaline phosphatase (Weiss et al., *Proc. Natl. Acad. Sci. USA* 83:7182–7186 [1986]). For general reviews on such polypeptides see M. G. Low, *Biochem. J.* 244:1–13 (1987) and M. G. Low et al. *TIBS* 11:212–215 (1986).

In some instances, e.g. where the C-terminus of the heterologous polypeptide contains an active site or immune epitope which is to be sterically free, then it will be desirable to introduce a spacer polypeptide between the C-terminus of the heterologous polypeptide and the GPI signal domain. This optimally will be additional sequences from the anchor domain donor polypeptide, for example about from 10 to 50 residues N-terminal to the anchor domain, but also may be artificial sequences.

The amino acid sequences imputed from DNAs encoding GPI signal domains exhibit little or no sequence homology beyond a C-terminal sequence of about from 10 to 20 residues containing uncharged, hydrophobic residues (leucine, glycine, threonine, valine, methionine, isoleucine and/or phenylalanine). However, this notwithstanding, the phospholipid anchor domain is embraced within the region immediately N-terminal to the hydrophobic sequence and is readily identifiable on this basis. Those skilled in the art will be capable of refining the optional sequence of the phospholipid anchor domain.

As noted above, the character and identity of polypeptides to be linked to the phospholipid anchor domain are unlimited. Their choice will depend upon the therapeutic or diagnostic objective which is intended. All that is necessary is that the fused polypeptide exhibit the desired biological activity of the unfused polypeptide prior to its expression as a hybrid with a phospholipid anchor domain. The polypeptide may be of any length, from about 4 residues to thousands, and includes enzymes, hormones, antigens and the like.

The expression hosts for these fusions are cells capable of processing the GPI signal and attaching the GPI anchor. Such cells preferably are mammalian continuous cell lines as described elsewhere herein, most preferably DHFR·CHO or 293 cells.

The fused polypeptide is employed together with the cells in which it is produced, i.e., without recovery from the expression hosts, in the immunogen utility described above. In other instances, e.g. adsorption of the fusion to hydrophobic affinity matrices in connection with preparing diagnostic kits, the fusion is recovered from the expression host prior to its use. The fusion is recovered from host cell membranes by preparing cell membrane extracts in substantially the same fashion as mDAF or other anchored polypeptides heretofore have been isolated. Other methods for obtaining preparations of membrane anchored polypeptides such as receptors also are known and are adaptable for use in recovering the fusions described herein. Typically, the host cell membranes are separated from the cytoplasm, solubilized with nonionic detergent, and the fusion recovered by adsorption on immunoaffinity, substrate or ligand affinity columns. The fusions will be recovered as polypeptides containing the heterologous polypeptide with a C-terminally linked GPI-anchor glycophospholipid. Note that the fusion protein will be recovered in a form which is free of the C-terminal hydrophobic sequence present before processing of the fusion and substitution with the glycophospholipid.

Fusions which are purified free of host cell membranes are useful as therapeutic compositions. For example, a fusion containing a plasminogen activator enzyme such as urokinase or tissue plasminogen activator is fused to a GPI signal domain and administered in therapeutic compositions to patients experiencing myocardial infarcts or other disorders accompanied by undesirable blood clots. Preferably, the enzyme is fused at its C-terminus to the N-terminus of the GPI signal domain. It will be understood that the GPI signal domain specifies attachment of a GPI glycophospholipid, substituted at a carboxyl group of the C-terminal amino acid residue. The fused plasminogen activator will insert into blood cells and vasculature where it will be most effective at activating plasminogen and will not be subject to removal from the blood stream by degradative processes such as those performed by the liver or spleen, thereby extending the half life of the enzyme and targeting it more directly to the desired therapeutic site.

These advantages are applicable to any polypeptide which desirably functions at cell membrane surfaces, particularly cells readily accessible to the circulatory system such as hematopoietic cells or vascular epithelia. For example, patients suffering from disorders characterized by the absence of a critical enzyme activity, as for example in inborn errors of metabolism, are treated by an infusion of the enzyme in question fused to a phospholipid anchor domain. The kinetics of synthesis and delivery to the cells of the required metabolite are improved over simply infusing the metabolite. This approach also provides many advantages over somatic cell transformation as an alternative method to providing the metabolite. The fusion is injected into the cerebrospinal fluid, e.g., in order to address metabolic deficiencies of brain cells, or into the lymph system or blood stream as required to optimally target other tissue or organ system-specific disorders.

The novel fusions are particularly useful in overcoming defects or deficiencies within the immune system, particularly in the process of antigen presentation. An antigen to which it is desired to modulate an immune response is synthesized as a fusion with a GPI signal domain and the resultant GPI-linked polypeptide administered under conditions and in a dosage determined to produce the desired effect. There is no limit on the choice of antigen, but the fusion must preserve the relevant epitope(s) of the antigen. This is readily determined by conventional competitive-type immunoassay using antibody raised against the native antigen and labeled native antigen, in accordance with methods well known to those skilled in the art. Antigen fusions also are useful in in vitro diagnostics as described above or in affinity chromatography.

The novel fusions herein optionally are formulated into liposomes or other lipid membrane carriers. This is readily accomplished by mixing a solution of the GPI-linked fusion protein with a preformed liposomal suspension and incubating until the insertion of the fusions into the liposomal bilayer. Alternatively, the fusions are admixed with the aqueous solution used in the preparation of the liposomes. Alternatively, the fusions are formulated into conventional pharmacologically acceptable vehicles as described below for mDAF. Since the fusions bear hydrophobic substituent they can be formulated with pharmacologically acceptable detergents such as Tween 20 or polyethylene glycol (PEG), or with serum albumin. Such liposome fusions are especially useful in the treatment of infectious diseases and cancer therapy. For example, GPI-linked CD4 (CD4/DAP) can be generated by fusing the extracellular domain of CD4 to the GPI signal domain of DAF. The CD4/DAF may be linked to a liposome within which a toxic drug has been packaged, and then used to target the construct to HIV infected cells which express gp120 on their surfaces. Similar GPI fusions to ligands or antibodies can be used to target liposome containing toxic agent to cancer cells having receptors or antigens which specifically bind to the ligands or antibodies.

The following disclosure relating to DAF is to be considered as applying with equal effect to the glycophospholipid fusions described immediately infra, except as noted that the fusions should be produced in higher eukaryotes.

Most deletions and insertions, and substitutions in particular, will not produce radical changes in the characteristics of the DAF molecule. However, when it is difficult to predict the exact effect of the substitution, deletion or insertion in advance of doing so, for example when modifying DAF receptor binding domain or an immune epitope, one skilled in the art will appreciate that the effect will be evaluated by routine screening assays. For example, a variant typically is made by site specific mutagenesis of the native DAF-encoding nucleic acid, expression of the variant nucleic acid in recombinant cell culture and, optionally, purification from the cell culture for example by immunoaffinity adsorption on a rabbit polyclonal anti-DAF column (in order to adsorb the variant by at least one remaining immune epitope). The activity of the cell lysate or purified DAP variant is then screened in a suitable screening assay for the desired characteristic. For example, a change in the immunological character of the DAF, such as affinity for a given antibody, is measured by a competitive-type immunoassay. Changes in immunomodulator activity are measured by the C4b2a assay, although as more becomes known about the functions in vivo of sDAF and mDAF other assays will become useful in such screening. Modifications of such protein properties as redox or thermal stability, hydrophobicity, susceptibility to proteolytic degradation, or the tendency to aggregate with carriers or into multimers are assayed by methods well known to the artisan.

DAF from other species than humans, e.g. bovine, equine, ovine, porcine and the like is included within the scope hereof.

DAF preferably is made by synthesis in recombinant cell culture. In order to do so, it is first necessary to secure nucleic acid that encodes DAF. The inventors encountered considerable hardship in attempting to identify any nucleic acid encoding DAF. The sequence of the human mDNA encoding DAF that was ultimately determined is shown in FIG. 1. As noted above, study of cDNAs from hela cells led to the identification of cDNA encoding sDAF, shown in FIG. 2. Once this DNA has been identified it is a straight-forward matter for those skilled in the art to obtain it by nucleic acid hybridization to genomic libraries of human DNA or, if it is desired to obtain DNA encoding the DAF of another animal species, then by hybridization of DNA libraries from cells of that species. The hybridization analysis is now straightforward because FIGS. 1 and 2 enable the preparation of very long synthetic probes that are perfect or nearly perfect matches for the target DNA.

It is possible that the CDNA or genomic library selected as the source for the DAF nucleic acid will not contain a single clone encoding the full length DAF, only partial clones. These partial clones and fragments are readily assembled into a full length DNA by cleaving the partial clones at selected restriction sites in overlapping sections, recovering each of the desired fragments and ligating them in the proper order and orientation. If necessary, oligonucleotides are prepared to supply any missing sequences.

The DAF-encoding nucleic acid is then ligated into a replicable vector for further cloning or for expression. Vectors are useful for performing two functions in collaboration with compatible host cells (a host-vector system). One function is to facilitate the cloning of the nucleic acid that encodes the DAF, i.e., to produce usable quantities of the nucleic acid. The other function is to direct the expression of DAF. One or both of these functions are performed by the vector-host system. The vectors will contain different components depending upon the function they are to perform as well as the host cell that is selected for cloning or expression.

Each vector will contain nucleic acid that encodes DAF as described above. Typically, this will be DNA that encodes the DAF in its mature form linked at its amino terminus to a secretion signal. This secretion signal preferably is the DAF presequence that normally directs the secretion of DAF from human cells in vivo. However, suitable secretion signals also include signals from other animal DAFs, viral signals or signals from secreted polypeptides of the same or related species.

Expression and cloning vectors contain a nucleic acid sequence that enables the vector to replicate in one or more selected host cells. Generally, in cloning vectors this sequence is one that enables the vector to replicate independently of the host chromosomes, and includes origins of replication or autonomously replicating sequences. Such sequences are well-known for a variety of bacteria, yeast and viruses. The origin of replication from the well-known plasmid pBR322 is suitable for most gram negative bacteria, the 2μ plasmid origin for yeast and various viral origins (SV40, polyoma, adenovirus, VSV or BPV) are useful for cloning vectors in mammalian cells. Origins are not needed for mammalian expression vectors (the SV40 origin is used in the Examples only because it contains the early promoter). Most expression vectors are "shuttles" vectors, i.e. they are capable of replication in at least one class of organisms but can be transfected into another organism for expression. For example, a vector is cloned in E. coli and then the same vector is transfected into yeast or mammalian cells for expression even though it is not capable of replicating independently of the host cell chromosome.

DNA also is cloned by insertion into the host genome. This is readily accomplished with bacillus species, for example, by including in the vector a DNA sequence that is complementary to a sequence found in bacillus genomic DNA. Transfection of bacillus with this vector results in homologous recombination with the genome and insertion of DAF DNA. However, the recovery of genomic DNA encoding DAF is more complex than that of an exogenously replicated vector because restriction enzyme digestion is required to excise the DAF DNA.

Generally, DNA is inserted into a host genome for purposes of preparing a stable cell line or microbe for DAF expression.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

A suitable selection gene for use in yeast is the t g gene present in the yeast plasmid YRp7 (Stinchcomb et al., Nature 282:39 [1979]; Kingsman et al., Gene 7:141 [1979]; or Tschemper et al., Gene 10:157 [1980]). The trp1 gene provides a selection marker for a mutant strain of yeast lacking the ability to grow in tryptophan, for example ATCC No. 44076 or PEP4-1 (Jones, Genetics 85:12 [1977]). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR) or thymidine kinase. Such markers enable the identification of cells which were competent to take up the DAF nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes DAF. Amplification is the process by which genes in greater demand for the production of a protein critical for growth are reiterated in tandem within the chromosomes of successive generations of recombinant cells. Increased quantities of DAP are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, Proc. Natl. Acad. Sci. USA 77:4216 (1980). A particularly useful DHFR is a mutant DHFR that is highly resistant to methotrexate (MTX) (EP 117,060A). This selection agent can be used with any otherwise suitable host, e.g. ATCC No. CCL61 CHO—K1), notwithstanding the presence of endogenous DHFR. The DHFR and DAF-encoding DNA then is amplified by exposure to an agent MTX that inactivates the DHFR. One ensures that the cell requires more DHFR (and consequently amplifies all exogenous DNA) by selecting only for cells that can grow in successive rounds of increasing MTX concentration.

Other methods, vectors and host cells suitable for adaptation to the synthesis of the hybrid receptor in recombinant vertebrate cell culture are described in M. J. Gething et al., Nature 293:620–625 (1981); N. Mantei et al., Nature 281:40–46 (1979); and A. Levinson et al., EP 117,060A and 117,058A. A particularly useful starting plasmid for mammalian cell culture expression of DAF is pE342.HBV E400.D22 (also called pE348HBVE400D22, EP 117,058A).

Expression vectors, unlike cloning vectors, should contain a promoter which is recognized by the host organism and is operably linked to the DAF nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DAF-encoding DNA by removing them from their gene of origin by restriction enzyme digestion, followed by insertion 5' to the start codon for DAF. This is not to say that the genomic DAF promoter is not usable. However, heterologous promoters generally will result in greater transcription and higher yields of expressed DAF.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exist then synthetic oligonucleotide adaptors or linkers are used in accord with conventional practice.

Promoters suitable for use with prokaryotic hosts include the β-lactamase and lactose promoter systems (Chang et al., Nature 275:615 [1978]; and Goeddel et al., Nature 281:544 [1979]), alkaline phosphatase, a tryptophan (trp) promoter system (Goeddel, Nucleic Acids Res. 8:4057 [1980]and EPO Appln. Publ. No. 36,776) and hybrid promoters such as the tac promoter (H. de Boer et al., Proc. Natl. Acad. Sci. USA 80:21–25 [1983]). However, other known bacterial promoters are suitable. Their nucleotide sequences have been published, thereby enabling a skilled worker operably to ligate them to DNA encoding DAP (Siebenlist et al., Cell 20:269 [1980]) using linkers or adaptors to supply any required restriction sites. Promoters for use in bacterial systems also will contain a Shine-Dalgarno (S.D.) sequence operably linked to the DNA encoding DAP.

Suitable promoting sequences for use with yeast hosts include the promoters for 3-phosphoglycerate kinase (Hitzeman et al., J. Biol. Chem, 255:2073 [1980]) or other glycolytic enzymes (Hess et al., J. Adv. Enzyme Rep. 7:149 [1968]; and Holland, Biochemistry 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

DAF transcription from vectors in mammalian host cells is controlled by promoters obtained from the genomes of viruses such as polyoma, cytomnegalovirus, adenovirus, retroviruses, hepatitis-B virus and most preferably Simian Virus 40 (SV40), or from heterologous mammalian promoters, e.g. the actin promoter. The early and late promoters of the SV40 virus are conveniently obtained as an SV40 restriction fragment which also contains the SV40 viral origin of replication (Fiers et al., Nature 273:113 [1978]). Of course, promoters from the host cell or related species also are useful herein.

Transcription of DAF-encoding DNA by higher eukaryotes is increased by inserting an enhancer sequence into the vector. An enhancer is a nucleotide sequence, usually about from 10–300 bp, that acts on a promoter to increase its transcription and does so in a manner that is relatively orientation and position independent. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenoviral enhancers. The enhancer may be spliced into the vector at a position 5' or 3' to the DAF-encoding sequence, but is preferably located at a site 5' from the promoter.

Expression vectors used in eukaryotic host cells (yeast, fungi, insect, plant, animal, human or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain regions that are transcribed as polyadenylated segments in the untranslated portion of the mRNA encoding DAF. The 3' untranslated regions also include transcription termination sites.

Suitable host cells for cloning or expressing the vectors herein are prokaryotes, yeast or higher eukaryotic cells. Prokaryotes include gram negative or gram positive organisms, for example E. coli or bacilli. A preferred cloning host is E coli 294 (ATCC 31,446) although other gram negative or gram positive prokaryotes such as E coli B, E coli X1776 (ATCC 31,537), E. coli W3110 (ATCC 27,325), pseudomonas species, or Serratia marcesans are suitable.

In addition to prokaryotes, eukaryotic microbes such as filamentous fungi or yeast are suitable hosts for DAF-encoding vectors. *Saccharomyces cerevisiae*, or common baker's yeast, is the most commonly used among lower eukaryotic host microorganisms. However, a number of other genera, species and strains are commonly available and useful herein.

The preferred host cells for the expression of DAF are cells derived from multicellular organisms. DAF's large size, together with its intramolecular disulfide bond(s) and, in the case of mDAF, its unique post-translational processing, suggests that the host cell will optimally be of a higher phylogenetic order than the microbes if one is to expect the recombinant protein to demonstrate optimal conformational fidelity to native DAF. In addition, it may be desirable to glycosylate DAF. All of these functions can be best performed by higher eukaryotic cells. In principle, any higher eukaryotic cell culture is workable, whether from vertebrate or invertebrate culture, although cells from mammals such as humans are preferred. Propagation of such cells in culture is per se well known. See *Tissue Culture*, Academic Press, Kruse and Patterson, editors (1973). Examples of useful mammalian host cell lines are VERO and HeLa cells, Chinese hamster ovary cell lines, the WI38, BHK, COS-7, MDCK cell lines and human embryonic kidney cell line 293.

Host cells are transformed with the above-described expression or cloning vectors and cultured in conventional nutrient media modified as is appropriate for inducing promoters or selecting transformants containing amplified genes. The culture conditions, such as temperature, pH and the like, suitably are those previously used with the host cell selected for cloning or expression, as the case may be, and will be apparent to the ordinary artisan.

sDAF preferably is recovered from the culture medium as a secreted protein, although it also may be recovered from host cell lysates when directly expressed without a secretory signal. As a first step, the culture medium or lysate is centrifuged to remove particulate cell debris. DAF also is purified from contaminant soluble proteins for example by adsorption on a section column, e.g. ConA, election, adsorption on an anti-sDAF or anti-mDAF immunoaffinity column and elution therefrom. Alternatively, other processes such as chromatography on alkyl Sepharose, silica or an anion or cation exchange resin or gel electrophoresis are used to separate the sDAF from contaminants. mDAF is recovered from transformant cell membranes using the method of Medof et al. (1984. Id.). mDAF variants in which the hydrophobic transmembrane region and/or the mDAF phosphatidylinositol-binding residue are deleted or substituted are recovered in the same fashion as sDAF, although variants in which the transmembrane region remains intact also are recovered from transformant cell membranes.

Since native DAF has a tendency to aggregate under some conditions it may be useful to stabilize the aggregative state of the multimers by providing in the separations a minor amount of a nonionic surfactant such as Tween or polyethylene glycol. A protease inhibitor such as PMSF also may be useful to inhibit proteolytic degradation during purification, and antibiotics may be included to prevent the growth of adventitious contaminants.

One skilled in the art will appreciate that purification methods suitable for native DAF may require modification to account for changes in the character of DAF or its variants upon expression in recombinant cell culture. For example, a DAF polypeptide produced in prokaryotic cell culture will not adsorb to Con-A Sepharose because it will be unglycosylated. In this case, other methods such as gel electrophoresis, ion exchange or immunoaffinity purification should be employed. Similarly, sDAF lipid-free C-terminal ADAF variants will not adsorb as readily to hydrophobic adsorbents as does mDAF. Appropriate purification methods will be apparent to the artisan, depending upon the characteristics of the particular recombinant DAF.

DAF is prepared as a nontoxic salt with such ions as sodium, potassium, phosphate, chloride and the like. Generally, DAF is stored in phosphate buffered saline or may be lyophilized in the presence of an excipient including sugar alcohols, e.g. mannitol or sorbitol; monosaccharides, e.g., glucose, mannose, galactose or fructose; oligosaccharides such as maltose, lactose or sucrose; and proteins such as human serum albumin.

The foregoing excipients also may contribute to the stability of DAF to inactivation or precipitation upon aqueous storage, and may be used together with other stabilizers which are conventional per se. Such stabilizers include chelating agents, e.g. EDTA; antioxidants such as ascorbate or dithiothreitol; amino acids; and nonionic surfactants such as polyethylene glycol or block copolymers of polyethylene and polypropylene glycol.

DAF is administered to humans or animals in order to ameliorate various disorders stemming from immune dysfunction or misdirection, particularly defects in the humoral immune response. Examples include PNH, inflammatory conditions such as inflammatory bowel disease (colitis), rheumatoid arthritis, allograft rejection and the like. Treatment with DAF should be instituted early in the development of such disorders.

Therapeutic DAF compositions will contain a therapeutically effective dose of DAF in a pharmacologically acceptable carrier. The dose, carrier and route of administration selected will depend, among other factors; upon the disorder or condition to be treated, the condition of the patient, the desired route of administration, and the activity of the selected DAF variant. This is readily determined and monitored by the physician during the course of therapy.

The carrier for infusion or injection of DAF is a sterile isotonic aqueous solution, for example saline for injection or 5% dextrose. These preparations are injected or infused by intranasal, subcutaneous, intravenous, intraperitoneal or other conventional routes of administration. Preparations also are injected into the synovial fluid of arthritic joints.

DAF also is provided in a sustained release carrier. Suitable examples include semipermeable polymer matrices in the form of shaped articles, e.g. suppositories, or microcapsules. Implantable or microcapsules sustained release matrices include polylactides (U.S. Pat. No. 3,773,919, EP 58,481) copolymers of L-glutamic acid and gamma ethyl-L-glutamate (Sidman et al., *Biopolymers* 22(1):547–556 [1983]), poly (2-hydroxyethyl-methacrylate) (R. Langer et al., *J. Biomed. Mater. Res.* 15:167–277[1981] and R. Langer, *Chem. Tech.* 12:98–105[1982]), ethylene vinyl acetate (R. Langer et al., *Id.*), or poly-D-(-)-3-Hydroxybutyric acid (EP 133,988A). Sustained release DAF compositions also include liposomally entrapped DAF. Liposomes containing DAF are prepared by methods known per se: DE 3,218, 121A; Epstein et al. *Proc. Natl. Acad. Sci. USA* 82:3688–3692[1985]; Hwang et al., *Proc. Natl. Acad. Sci. USA* 77:4030–4034[1980]; EP 52322A; EP 36676A; EP 88046A; EP 143949A; EP 142641A; Japanese patent application 83-118008; U.S. Pat. Nos. 4,485,045 and 4,544,545; and EP 102,324A.

Ordinarily the liposomes are of the small (about 200–800 Angstroms) unilamelar type in which the lipid content is greater than about 30 mol. % cholesterol, the selected proportion being adjusted for the optimal rate of DAF leakage.

Sustained release DAF preparations are implanted or injected into proximity to the site of inflammation or therapy, for example adjacent to arthritic joints or inflamed intestinal tissue.

Polyclonal rabbit or murine antisera raised against DAF is one described by Medof et al. (1984, Id.). Antisera are employed for immunoaffinity purification or DAF and in an ELISA assay for DAF. Antibody specific for the unique C-terminus of sDAF is made by immunizing an animal against an immunogenic sDAF conjugate, e.g. an immunogenic fusion made in recombinant cell culture as described elsewhere herein, and thereafter screening for the presence of anti-sDAF titer by passing the antiserum through a column of immobilized mDAF in order to adsorb antibodies directed against mDAF epitopes, incubating the unadsorbed antiserum in the presence of $^{125}$I-sDAF (prepared in substantially the same fashion as $^{125}$I-mDAF, Medof et al., 1984, Id.) to permit the unique sDAF epitopes to bind to the anti-sDAF antibodies in the unadsorbed antiserum, and determining the amount of unbound $^{125}$I-sDAF, e.g. by adsorption on protein-A Sepharose.

The sDAF-specific antibodies in such antisera are prepared by adsorption as immobilized mDAF, recovery of the unadsorbed fraction, adsorption on immobilized ADAF and elution with pH 4–6 buffer to recover the sDAF-specific antibodies substantially free of mDAF antibodies. Alternatively, spleen cells from immunized animals showing anti-sDAF neutralizing titer are recovered and fused to myeloma cells or are transformed with EB virus in known fashion in order to prepare monoclonal sDAF-specific antibodies.

Neutralizing antibodies against DAF are useful when conjugated to immunogenic polypeptides as immunogens for raising anti-idiotypic antibodies having DAF activity. Such anti-idiotypic antibodies are useful for the same diagnostic and therapeutic purposes as DAF.

In order to simplify the Examples certain frequently occurring methods will be referenced by shorthand phrases.

"Plasmids" are designated by a lower case "p" preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the micro-organism from which each restriction enzyme originally was obtained and then a number designating the particular enzyme. In general, about 1 μg of plasmid or DNA fragment is used with about 2 units of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133–134).

"Filling" or "blunting" refers to the procedure by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 μg of the target DNA in 10 mM Mg Cl$_2$, 1 mM dithiothreitol, 50 mM NaCl, 10 mM Tris (pH 7.5) buffer at about 37° C. in the presence of 8 units of the Klenow fragment of DNA polymerase I and 250 mM of each of the four deoxynucleoside triphosphates. The incubation generally is terminated after 30 min. by phenol and chloroform extraction and ethanol precipitation.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9:6103–6114 [1981], and D. Goeddel et al., *Nucleic Acids Res.* 8:4057[1980].

"Northern" blotting is a method by which the presence of a cellular mRNA is confirmed by hybridization to a known, labelled oligonucleotide or DNA fragment. For the purposes herein, unless otherwise provided, Northern analysis shall mean electrophoretic separation of the mRNA on 1 percent agarose in the presence of a denaturant (e.g., about 7% formaldehyde), transfer to nitrocellulose hybridization to the labelled fragment as described by T. Maniatis et al., Id., p. 202.

"Transformation" means introducing DNA into an organism so that the DNA is replicable, either as an extrachromosomal element or chromosomal integrant. Unless otherwise provided, the method used herein for transformation of i E. coliis the CaCl$_2$ method of Mandel et al., *J. Mol. Biol.* 53:154 (1970).

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., *Id*. P. 90, may be used.

"Oligonucleotides" are short length single or double stranded polydeoxynucleotides which are chemically synthesized by known methods and then purified on polyacrylamide gels.

The following examples are intended to merely illustrate the best mode now known for practicing the invention, but the invention is not to be considered limited thereto.

All references cited herein are expressly incorporated by reference in their entirety.

EXAMPLE 1

Identification of cDNA clones encoding DAF Cloning of human DAF

Human DAF was purified to homogeneity and 23 amino acids of N-terminal sequence were determined. Five of these were ambiguous.

A 69mer oligonucleotide probe based on this amino acid sequence was synthesized in vitro: The $^{32}$P-labelled (Kinased) probe had the following nucleotide sequence:
GCTGAGCACCTGCCCCTGATGTGC-
CCAATGCCCAGCCTGCCCTGGAGGGCAAGA AAC-
CCTTCCCTG A HeLa cell λ cDNA library (approx. 1×10$^6$ recombinants) was screened under low stringency conditions with this 69mer. Only one DAF clone (λ21) was identified, together with 6 false positives (by sequencing, these turned out to have limited nucleic acid homology with the probe, but a totally different amino and sequence). λ21 contained an insert encoding the sequence:

AspCysGlyLeuProProAspValProA-
snAlaGlnProAlaLeuGluGly<u>ArgThrSer</u>PheProGlu
wherein the underlined residues differed from those identified by amino terminal sequencing.

The initial DAF clone (clone λ21) was 1395 bp in length and contained a poly A tail but was missing the initiator methionine.

To determine the size of DAF MM a Northern bolt containing Hela cell Poly A+RNA was screened 32p-labelled with DAF λ21. This probe hybridized to two messages of sizes approximately 1500bp and 2,000 bp. These were of roughly equal intensity.

To identify longer DAF clones with extensions at either of the 5' or 3' ends, we isolated 2 small restriction fragments from the 5' and 3' ends of λ21 as follows:

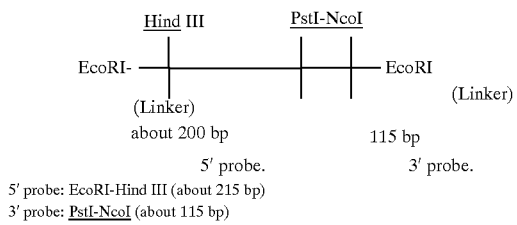

5' probe: EcoRI-Hind III (about 215 bp)
3' probe: <u>PstI-NcoI</u> (about 115 bp)

These probes were labelled with $^{32}$P and used to rescreened the Hela CDNA library for additional DAF—encoding clones. Two more clones were identified, DAF λ41 and DAF λ47. These hybridized to both probes and were longer than the DAF λ21 insert at approximately 2,000 bp and 2,200 bp respectively. Both of these clones contained about 780 bp of additional 3' untranslated sequence before the poly A tail. The 3'-untranslated sequence of the DAF gene contains a number of polyadenylation signals (AATAAA) and it appears that either an upstream of a downstream signal can be used to generate either the approx. 1,500 bp or the approx. 2,000 bp MRNAS.

At the 5' end, clone DAF λ41 was 55 bp longer than DAF λ21 and included an ATG for translation initiation. Clone DAF λ47 was 93 bp shorter than DAF λ21 at the 5' end.

Clone DAF λ33 also was identified, but it only hybridized to the 5' probe. This clone was 71 bp longer than DAF λ21 at the 5' end, and therefore represented the longest extension in the 5' direction.

DAF λ21 and DAF λ41 were completely overlapping in the coding region of the protein and encoded a protein of 440 amino acids. DAF λ47 and DAF λ33 contained an apparent 'deletion' of 118 bp of coding region with respect to DAF λ21 and DAF λ41. On closer inspection it appeared that DAF λ21 and DAF λ41 contained an unspliced (unremoved) intron of 118 bp. Subsequently two more clones were identified, DAF λ35 and DAF λ37, one of which contains the same intron and one of which does not.

The frequency with which the unspliced form is present in the library (3 out of 6 clones) suggests that it is unlikely the unspliced clones represents improperly spliced message. Rather, there appear to be two forms of the DAF protein. These 2 forms are identical at amino acid positions 1–327, while having different C-terminal sequences. The unspliced form contains an additional 79 amino acids, the spliced form contains an additional 20 amino acids. Since the splice produces a change in reading frame there is no homology between the 2 proteins at the C-terminii.

From the hydropathy plots of tie 2 DAF proteins, and from a comparison with the well-characterized Thy-1 membrane-bound glycoprotein, it is concluded that the spliced DAF CDNA directs synthesis of membrane-bound DAF, while the unspliced version encodes a soluble form.

EXAMPLE 2

Expression of DAF In Recombinant Cell Culture

Clones DAF λ33,λ41 and λ47 from Example 1 were each subcloned into pUC19, a readily available cloning vector for *E.coli*, by digesting each of the λ clones with EcoRI, recovering the DAF inserts from each, digesting pUC19 with EcoRI, ligating the inserts into opened pUC19 and transforming *E.coli* 294 with the each ligation mixture. pUC1933, pUC1941 and pUC1947 were recovered from ampicillin resistant colonies.

pUC1933, pUC1941 and pUC1947 were each digested with EcoRI and HindIII and the fragments (I, II and III respectively) containing the 5' end of the DAF gene, and the 3' ends of the sDAF and mDAF genes, respectively, were recovered. pUC19 digested with FMRI was ligated to Fragments I and II in a three way ligation and pUC19sDAF was recovered from an ampicillin resistant *E.coli* colony. This was the subclone of the complete sDAF gene shown in FIGS. 2a–2c.

pUC19mDAF was constructed in the same way as pUC19sDAF except that Fragment III was used in place of Fragment II. This subclone contained the complete mDAF gene of FIGS. 1a–1c.

pE348HBVE400D22 (also pE342HBVE400D22, EP 117, 058A) is digested with HindIII such that the DHFR—containing fragment is recovered. The HindIII cohesive terminii are filled, the fragment digested with ClaI and the following fragment isolated

| DHFR | HBsAg Poly A | pML | SV40 ori |
|---|---|---|---|
| ClaI (blunt) (Fragment a, 4084 bp) | | | HindIII | pE348 MBV E400D22 also is digested with ClaI and SocII such that the 990 bp fragment containing the SV40 ori and HVsAg poly A sequence is recovered (Fragment b).

pUCsDAF and pUCmDAF were digested with EcoRI and each DAF—encoding fragment isolated (Fragments CII and CIII, respectively).

Fragments CII, a and b are ligated in a three way ligation and transfected into *E. coli* 294. pE348sDAF is recovered from an ampicillin resistant colony. It contains the sDAF gene in proper orientation 3' to the SV40 sDAF early promoter. The sDAF gene is under the control of the SV40 early promoter in an expression vector suitable for transformation into and methotrexate selection and amplification in a mammalian host cell.

pE348mDAF is constructed in the same way except that Fragment CIII is used.

An alternative expression vector is constructed by digesting p342E (Crowley et al., *Mol. Cell. Biol.* 3:44–55 [1983]) with EcoRI and HpaI, and the vector fragment recovered. Either of pUC19mDAF or pUC19sDAF are digested with AccI (for mDAF) or blunt XhoII (for sDAF), filled, digested with EcoRI and the DAF—encoding fragments recovered. The DAF fragments are ligated into the vector fragment and expression vectors recovered. This vector does not contain the DHFR gene, although cotransformation with pFDll (Simonsen et al., *Proc. Natl. Acad. Sci. USA* 80:2495–99 [1983]) will produce satisfactory results.

pE348mDAF or pE348sDAF are co-transfected into DHFR·CHO cells using conventional methods, inoculated into HAT medium and transformants selected by culture in media containing serial increases in methotrexate concentration to amplify the DHFR and DAF genes. A transformant clone is recovered that stably expresses DAF and secretes it into the culture medium. The sDAF is recovered from the medium by adsorption onto an immunoaffinity column containing protein-A sepharose immobilized rabbit polyclonal antibody to sDAF and elution with pH5 glycine buffer.

pE348mDAF is transformed into an amplified in DHFR⁻ CHO cells in the same way. mDAF is recovered by isolation from detergent lysates of host cell membranes in essentially the same fashion as mDAF has been recovered heretofore from red blood cell stroma.

EXAMPLE 3

Construction of a GPI Signal Anchor Domain Fusion

In this Example a fusion protein was constructed in which the last 37 amino acids of membrane DAF predicted by the spliced cDNA were fused in-frame to the C-terminus of a truncated form of the Herpes Simplex Virus Type 1 (HSV 1) glycoprotein D (gD-1) that ordinarily is constitutively secreted to the culture medium since it lacks the C-terminal membrane-spanning domain (Lasky et al., Bio/Technology 2:527 [1984]). A HIII—HinfI fragment encoding the first 300 amino acids of HSV gD-1 was ligated via a synthetic linker to a XmnI-EcoRV fragment encoding the C-terminus of DAF (residues 316–347). The synthetic HinfI-XmnI linker (5'-ATTCGCCAAATAAAGGAAGTGG-AACC) encoded amino acid 301 of gD-1 and amino acids 311–317 of DAF and created an in-frame fusion.

The DNA encoding the gD-1/DAP fusion protein was inserted into a mammalian expression vector between an RSV promoter and an SV40 polyadenylation sequence by excision of the CAT gene and insertion of the fusion DNA (Gorman et al., *Proc. Natl. Acad. Sci. USA* 19:6777[1982]) and transfected into CHO cells by the calcium-phosphate coprecipitation method (Wigler et al., *Proc. Natl. Acad. Sci. USA* 76:1373[1979]and Simonsen et al., *Proc. Natl. Acad. Sci. USA* 80:2495[1983]). Mouse dihydrofolate reductase cDNA provided a selectable marker for gene expression (Simonsen et al., *Proc. Natl. Acad. Sci. USA* 80:2495 [1983]). Stable cell lines derived from individual colonies were used for analysis. Cell lines expressing native gD-1 or truncated gD-1 were derived as described (Lasky et al., *Bio/Technology* 2:527 [1984] and Berman et al., *Science* 222:524[1983]). The resultant fusion protein (FIG. 3) contains the N-terminal 75% of gD-l (residues 1–300) including the signal sequence, and the C-terminal 10% (37 amino acids) of membrane DAF including the 20 amino acid segment that is divergent between the two predicted DAF proteins and 17 amino acids of adjacent common sequence. The gD-1/DAF fusion protein, native gD-1 (Berman et al., *Science* 222:524[1983]), and the truncated gD-1 (Lasky et al., *Bio/Technology* 2:527[1984]) were expressed in CHO cells and localized by indirect immunofluorescence. Internal labeling of permeabilized cells expressing either native gD-1 or the gD-1/DAF fusion showed similar localization of immunofluorescence in a perinuclear region, possibly the endoplasmic reticulum. Cells expressing truncated gD-1 showed intense fluorescence diffused throughout the cell cytoplasm. Immunofluorescence of intact (non-permeabilized) cells expressing full-length native gD-1 shows that this protein is expressed on the cell surface as expected from its transmembrane domain. In contrast, no surface labeling was detected in cells expressing the truncated (secreted) form of gD-1. Cells expressing the gD-1/ DAF fusion protein also show surface staining indicating that addition of the C-terminal domain of DAF redirects the secreted (truncated) gD-1 to the plasma membrane.

The C-terminal segment of DAF encoded by the gD-1/ DAF fusion contains a 17 amino acid hydrophobic region at the C-terminus which may act as a transient membrane anchor thought to be removed post-translationally and replaced with a GPI-anchor (Low, M. G., *Biochem. J.*244:1–13 [1987]; Cross, G. A. M. *Cell* 48:179–181 [1987]; and Caras, I. W. et al., *Nature* 325:545[1987]). The above experiments do not distinguish whether the fusion protein is anchored by a GPI anchor or by the 17 amino acid hydrophobic region. Therefore, to determine the nature of the attachment, CHO cells expressing either native gD-1 or gD/DAF fusion were incubated with purified phosphatidylinositol-specific phospholipase C (PI-PLC) from *Staphylococcus aureus* (Low, M. G., *Meth. Enzymol.* 71:741[1981]), and analyzed by indirect fluorescence and flow cytometry (FACS). Treatment with PI-PLC (which is free of proteolytic contaminants (Low et al., *Nature* 318:62 [1985]) resulted in a substantial reduction in the amount of gD-1/DAF on the cell surface as indicated by the marked decrease in relative cell fluorescence displayed on a log scale. Typically, 70–80% of the cell-surface gD-1/DAF was released by PI-PLC as indicated by quantitative FACS analysis. In contrast, full-length native gD-1 expressed on the cell surface was unaffected by treatment with PI-PLC.

The specificity of the release was further confirmed by the observation that the phospholipase C from either *Clostridium perfringens* or *Bacillus cereus*, which does not hydrolyze phosphotidylinositol (Little, C., *Meth. Enzymol.* 71:725[1981] and Takahashi, T. et al., *Meth. Enzymol.* 71:710[1981]), did not release gD-1/DAF from the plasma membrane.

The glycophospholipid (GPI) anchor of DAF contains ethanolamine and glucosamine in addition to phosphatidylinositol (Medof et al., *Biochemistry* 25:6740[1986]). The glycosylated phospholipid is thought to be linked to the protein through an amine bond between the terminal carboxyl group of the polypeptide and the amine group of ethanolamine (Low, M. G. Biochem. J. 244:1–13[1987] and Cross, G. A. M., *Cell* 48:179–181[1987]). To confirm that the gD-1/DAF fusion protein is anchored by such a structure cells were metabolically labelled with either [$^3$H] ethanolamine or [$^{35}$S] cysteine and the proteins analyzed by immunoprecipitation. Multiple forms of gD-1/DAF, a 37 kD species and at least two larger, highly diffuse species of approximately 46 kD and 52 kD, respectively, were detected by both polyclonal and monoclonal antibodies to HSV-1 only in cells expressing gD-1/DAF. Preliminary pulse-chase experiments and experiments with neuraminidase suggest that the 37 kD species is a precursor, while the larger species represent mature, highly glycosylated forms of the protein. A [$^3$H] Ethanolamine-labelled band corresponding to the 46 kD species is a precursor, while the larger species represent mature, highly glycosylated forms of the protein. [$^3$H] Ethanolamine-labeled bands corresponding to 46 kD and 52 kD species but not a 37 kD species were specifically detected in cells expressing gD-1/DAF. Attachment of the glycophospholipid anchor is thought to be an early event in the biosynthesis of lipid-anchored proteins (Medof et al., *Biochemistry* 25:6740[1986] and Berman et al. *Science* 222:524 [1983]). The absence of a [$^3$H] ethanolamine-labeled band corresponding to the 37 kD gD-1/DAP precursor may be due to the long pulse (16 h) used to label cells in this experiment. Native gD-1 was not labeled with [$^3$H] ethanolamine.

It was concluded that the gD-1/DAF fusion protein is linked to the plasma membrane via phosphatidylinositol. This conclusion is supported by the following evidence. First, gD-1/DAF on the cell surface was sensitive to digestion with highly purified phosphatidylinositol-specific phospholipase C while native gD-1 was unaffected. Second, broad specificity phospholipases were ineffective in releasing gD-1/DAP. Third, gD-1/DAF was specifically labeled by [3H] ethanolamine, a component of the glycophospholipid anchor. Thus, the information or "signals" necessary for directing the attachment of a phospholipid membrane anchor is contained within the C-terminal 37 amino acids of DAF. The concept that the C-terminal sequence plays a role in directing the attachment of lipid is supported by recent identification of multiple classes of the neural cell adhesion molecule (N-CAM) mRNA, presumably resulting from differential mRNA splicing. The different forms of N-CAM encoded by these mRNAs have different C-terminal domains, apparently resulting in membrane attachment either via a hydrophobic membrane-spanning domain, or via a phospholipid (Hemperly et al., *Proc. Natl. Acad. Sci. USA* 83:9822[1986]). Inspection of the C-terminal amino acid sequences available for PI-anchored proteins has revealed no obvious homology, the only common feature being the presence of a short hydrophobic peptide (15–20 residues) at the C-terminus predicted by the cDNA sequence. This hydrophobic peptide, which could serve as a transient membrane anchor, is presumed to be removed during processing (Low, M. G., *Biochem. J.* 244:1–13[1987] and Cross, G. A. M., *Cell* 48:179–181[1987]). The lack of sequence conservation in the C-terminal region of PI-anchored proteins suggests that the processing signal is conformational in character. Addition of a phospholipid membrane anchor by the means described above offers a novel mechanism for targeting soluble or secreted proteins to the cell surface membrane.

EXAMPLE 4

Attachment of Proteins To Liposomen Using A GPI-Anchor

In this example a glycophosphatidylinositol (GPI) membrane. anchor was used instead of chemical cross-linking to attach a biologically relevant protein of interest to liposomes. GPI-anchor attachment may be used, for example, to add a targeting function to the liposomes. The advantages of this approach are multifold. First, chemical manipulation of the protein of interest, which can be damaging and cause inactivation, is avoided. Second, the orientation of a GPI-anchored protein on the liposome surface is precise; i.e. the protein molecules will all be anchored at their COOH-termini via the GPI-anchor, with the ectodomain of the protein facing the aqueous environment. If the protein is a receptor or a ligand for a receptor, this arrangement would resemble the native state in which such proteins are normally attached to a cell surface with the ectodomain facing outwards. Third, preformed liposomes packaged with any molecule of choice can be used. Since the GPI-anchored proteins spontaneously incorporate into the lipid bilayer, attachment of the protein is extremely simple and easy to achieve. Fourth, a GPI-anchor can be added to potentially any recombinant secreted or membrane protein using a DNA sequence encoding a GPI-signal, such, as, for example, the COOH—terminal sequence of DAF.

A. Spontaneous incorporation of GPI-linked gp120 (gp120/DAF) into liposomes

Figure 5:
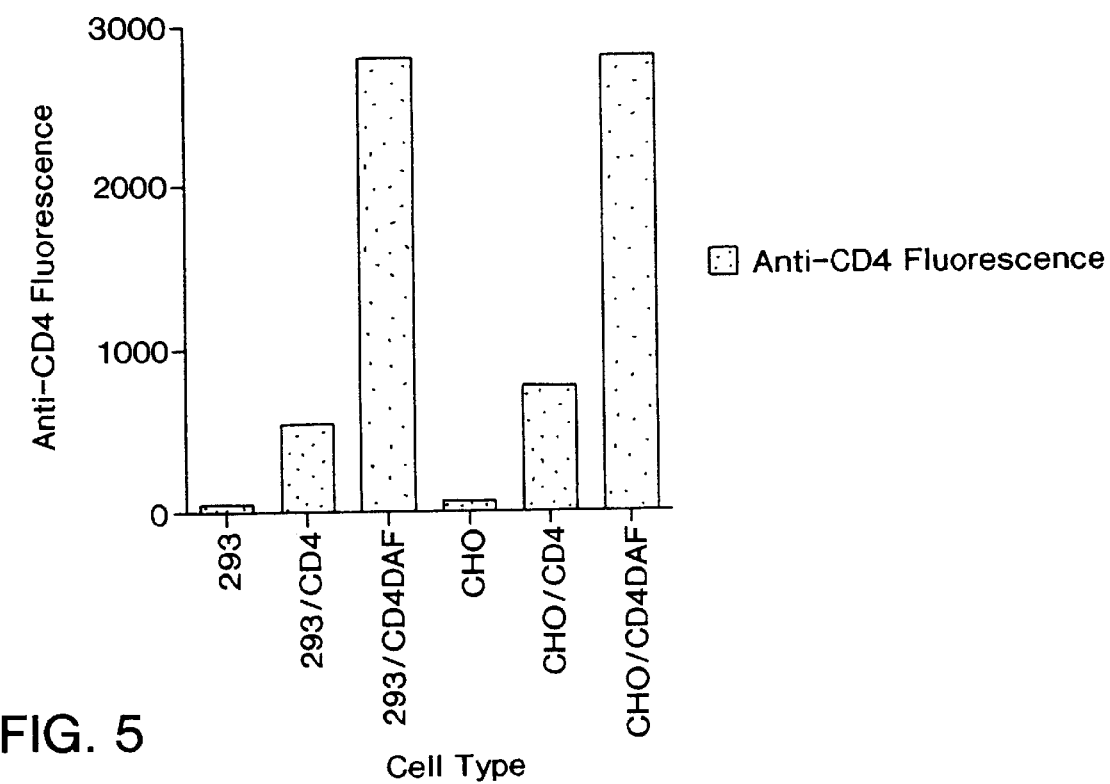
FIG. 5. is a graph depicting relative levels of CD4 on the surface of transfected 293 and CHO cells. CD4/DAF is a GPI-linked form of CD4 formed by expressing a CDNA encoding the extracellular domain of CD4 fused to the GPI signal domain of DAF. Nontransfected parental cells (293 or CHO), or cells transfected with CD4 or CD4/DAF as indicated, were incubated at 4° C. with an anti-CD4 mouse monoclonal antibody followed by fluorescein-labeled anti-mouse IgG. The cells were then washed and subjected to FACS analysis.
Figure 6:
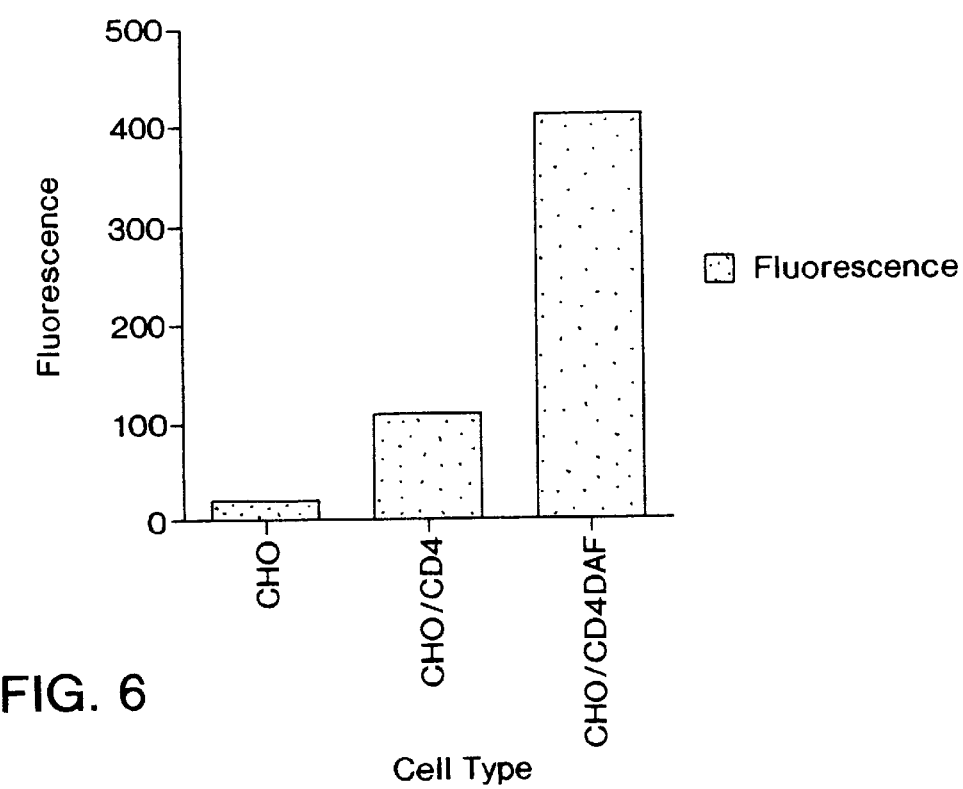
FIG. 6. is a graph depicting targeted binding of FITC-dextran-labeled liposomes to CHO cells expressing CD4. Preformed liposomes loaded with FITC-dextran were coated with gp120/DAF and then incubated at 4° C. for 1–2 h with parental CHO cells or with cells expressing CD4 or CD4DAF as indicated. The cells were then washed and analyzed by FACS.

Using standard DNA manipulation techniques, as described above, the fusion protein gp120/DAF was created. This fusion protein contains HIV-1 gp120 fused to the COOH-terminal 37 amino acids of DAF. When expressed in 293 or CHO cells, this construct produced GPI-linked gp120/DAF on the cell surface. Recombinant gp120/DAF was purified by affinity chromatography from the membranes of transfected 293 cells, following extraction with a detergent (either octylglucoside or CHAPS).

To demonstrate that the purified gp120/DAF spontaneously incorporates into liposomes, $^{125}$I-labeled gp120/DAF was mixed with $^{14}$C-labeled liposomes and then dialyzed against PBS to remove residual detergent. To separate liposome-associated gp120/DAF from non-associated gp120/DAP, the mixture was loaded onto a 3–25% sucrose gradient and centrifuged at 250,000×g for 4.5 h at 4° C. Fractions were then collected and analyzed for the presence of $^{125}$I-labeled gp120/DAF. A parallel gradient containing only $^{14}$C-labeled liposomes was analyzed to locate the position of the liposomes on the gradient. As shown in FIG. 4, the liposomes floated to the top of the gradient, and were recovered as a peak in fractions 2–4. Using defined protein molecular weight markers, a soluble 120kD protein ran towards the bottom of the gradient under these conditions. A peak of $^{125}$I-labeled gp120/DAF was recovered in fractions 2–4, indicating liposome-association (FIG. 4). Approximately 40% of the $^{125}$I-labeled gp120/DAF loaded on the gradient was recovered as liposome-associated protein. The remaining $^{125}$I-labeled gp120/DAF sedimented to the bottom of the gradient and remained irreversibly attached to the tube.

B. Interaction of gp120/ DAF-tagged liposomes with cells

To demonstrate that liposome-associated gp120/DAF can target liposomes to cells bearing the appropriate receptor (CD4), preformed liposomes loaded with a fluorescent marker (either FITC-dextran or carboxyfluorescein) were tagged with gp120/DAF as described above. These liposomes were then incubated at 4° C. with transfected 293 or CHO cells expressing either recombinant transmembrane CD4 (Genentech, Inc.) or recombinant GPI-linked CD4 (CD4DAF), or with nontransfected control cells that lack CD4. The cells were then washed to remove non-bound liposomes, and the amount of cell-associated fluorescence (a measure of the binding) was assessed using a fluorescence-activated cell sorter (FACS) (FIG. 5). In a parallel experiment, the cells were labeled with a fluorescent antibody to CD4, to provide a relative measure of the levels of CD4 on their surface. As shown in FIG. 6, gp120/DAF-tagged liposomes bound very weakly to nontransfected 293 or CHO cells that lack CD4. In contrast, these liposomes interacted strongly with cells expressing either native CD4 or CD4DAP. This result demonstrated (i) that gp120/DAP-tagged liposomes bound preferentially to cells that expressed the CD4 receptor on their surface, and (ii) that the level of CD4 on the cell surface was proportional to the level of binding.

C. Specificity of the interaction of gp120/DAF-tagged liposomes with cells

Figure 7:
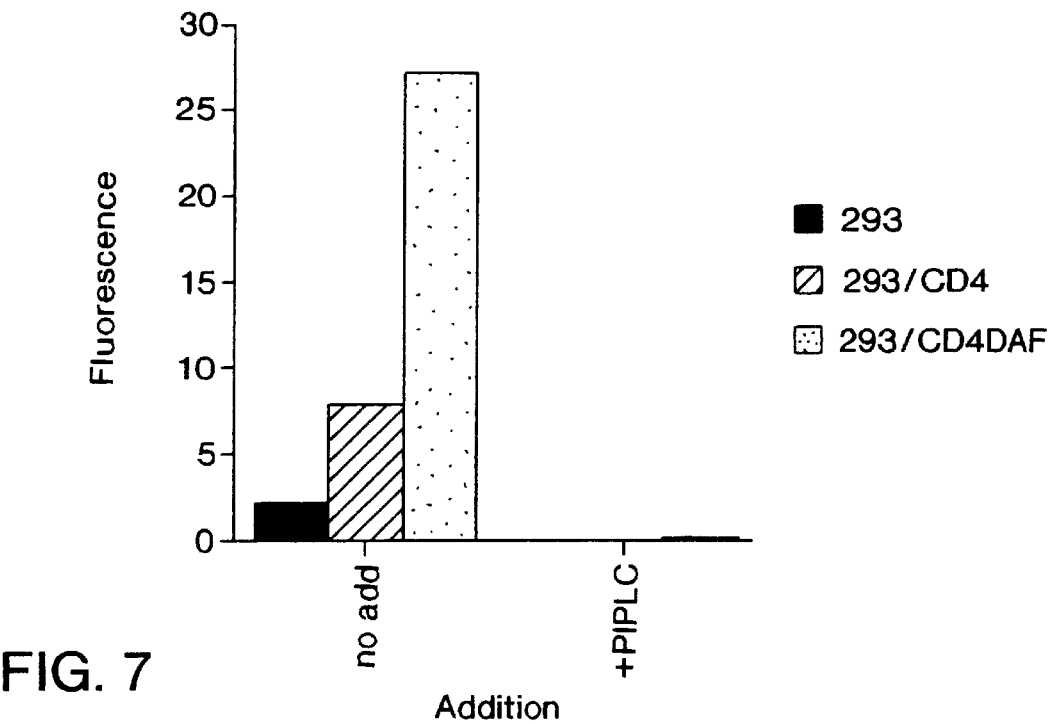
FIG. 7. is a graph depicting targeted binding of FITC-dextran-labeled liposomes to 293 cells expressing CD4 mediated by GPI-linked gp120/DAF. Preformed liposomes loaded with FITC-dextran and coated with gp120/DAF, were incubated at 4° C. with parental 293 cells or with 293 cells expressing CD4 or CD4DAF as indicated. The cells were then washed, and incubated at 4° C. in the presence or absence of PIPLC, and analyzed by FACS. PIPLC-treatment removed the FITC-labeled liposomes from the cell surface, indicating that attachment is mediated by a GPI-linked molecule.

The above result indicated that the liposome-cell interaction observed was mediated by the binding of gp120 to CD4. To provide further evidence for this concept, 293 cells were first incubated with carboxyfluorescein-loaded, gp120/DAF-tagged liposomes to allow binding, and then incubated with phosphatidylinositol-specific phospholipase C (PIPLC). As PIPLC specifically cleaves within the GPI-anchor, thereby severing gp120/DAF from the liposome surface, the GPI-linked molecule, CD4DAF, would also be released from the surface of cells expressing this molecule. FACS analysis showed that treatment with PIPLC removed bound liposomes from the surface of 293 cells expressing CD4, indicating that the binding was mediated by the GPI-linked molecule, gp120/DAF (FIG. 7).

Figure 8:
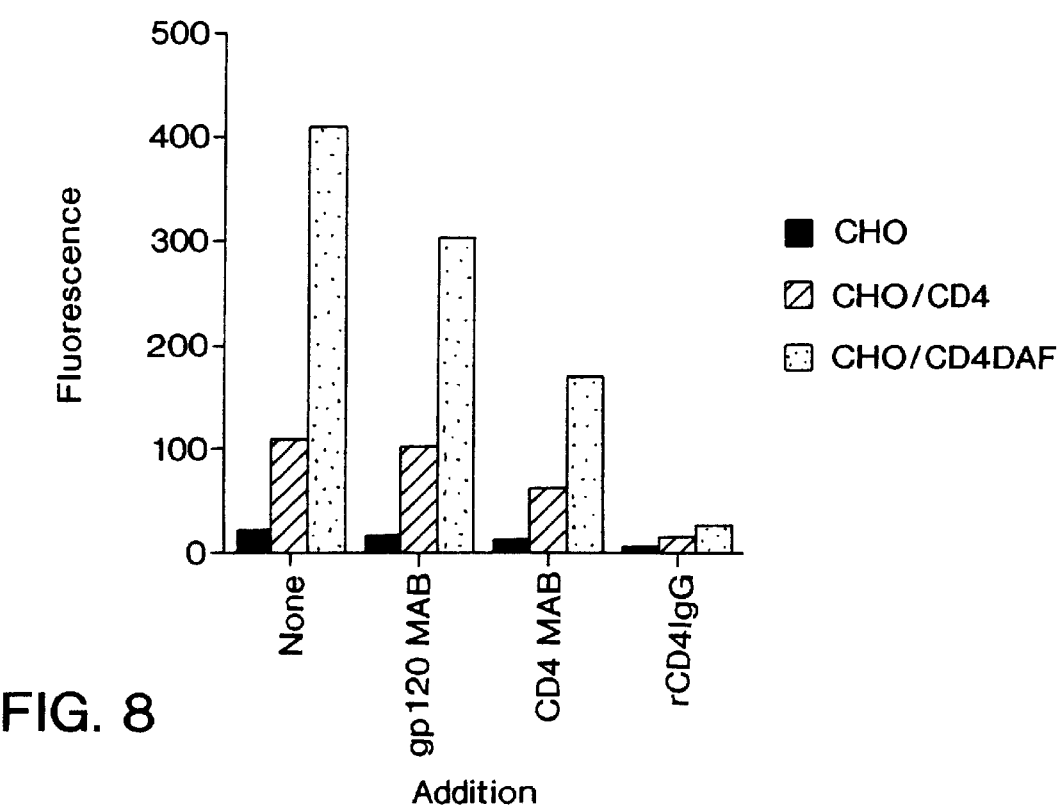
FIG. 8 is a graph depicting the targeted binding of FITC-dextran-labeled liposomes to cells. FITC-dextran-loaded liposomes coated with gp120/DAF, were incubated at 4° C. with CHO cells as indicated, in the presence of molecules that interfere with the binding of gp120 to CD4 (anti-CD4 or anti-gp120 monoclonal antibodies, or soluble CD4, denoted rCD4IgG). The cells were then washed and analyzed by FACS.

To further demonstrate that the liposome-cell interaction was mediated by the binding of gp120 to CD4, cells were incubated with liposomes in the presence of specific inhibitors of this interaction. As shown in FIG. 8, an excess of soluble CD4 (rCD4IgG, Genentech, Inc.) totally blocked the binding of the liposomes to cells expressing CD4 on their surface, indicating that CD4 was critical for the liposome-cell interaction. In addition, antibodies to gp120 or CD4 decreased the binding of liposomes to cells, confirming the involvement of gp120/DAF and CD4.

In summary, a GPI-linked molecule, gp120/DAF, when mixed with liposomes, spontaneously associated with the lipid bilayer. The liposome-associated gp120/daf could bind to cd4 on the surface of cells, and effectively targeted liposomes to cells that express the CD4 receptor.

What is claimed is:

1. An isolated nucleic acid molecule comprising a nucleic acid sequence encoding a decay accelerating factor (DAF) having an amino acid sequence shown in FIGS. 1A–D (SEQ ID NO:2) or FIGS. 2A–E (SEQ ID NO:4) or an antigenic fragment thereof.

2. The isolated nucleic acid molecule of claim 1 free of introns or flanking genomic DNA.

3. A method for making a recombinant host cell which is able to produce a polypeptide defined in claim 1 comprising transforming a host cell with the nucleic acid of claim 1.

4. A method of making a polypeptide defined in claim 1 comprising culturing a host cell possessing the nucleic acid of claim 1 so as to express the nucleic acid.

5. A vector comprising the nucleic acid of claim 1.

6. The vector of claim 5 wherein the DAF is a secreted DAF molecule (sDAF) having an amino acid sequence shown in FIGS. 2A–E (SEQ ID NO: 4) or an antigenic fragment thereof.

7. A host cell comprising the vector of claim 5.

8. The host cell of claim 7 which is a mammalian cell.

9. A method of using the vector of claim 5 comprising culturing a host cell possessing said vector so as to clone the nucleic acid.

10. An isolated nucleic acid molecule comprising a nucleic acid sequence encoding a DAF variant comprising one or more amino acid deletions from the amino acid sequence shown in FIGS. 1A–D (SEQ ID NO:2) or FIGS. 2A–E (SEQ ID NO:4) or an antigenic fragment thereof, wherein said amino acid deletions are selected from the group of deletions consisting of des-$Cys_{330}$, des-$Cys_{330}$–$Thr_{347}$, and des-$Thr_2$-$Gly_{327}$.

11. A vector comprising the nucleic acid molecule of claim 10.

12. A host cell comprising the vector of claim 11.

13. An isolated nucleic acid molecule comprising a nucleic acid sequence encoding a DAF variant comprising one or more amino acid substitutions within the amino acid sequence shown in FIGS. 1A–D (SEQ ID NO:2) or FIGS. 2A–E (SEQ ID NO:4) or an antigenic fragment thereof, wherein said amino acid substitutions are selected from the group consisting of $Cys_{330}$ 4 Met, $Cys_{330}$ 4 Ser, $Cys_2 \rightarrow Ser$, $Lys_{125}Lys_{126} \rightarrow Gln$, $Gly_{144} \rightarrow Pro$, $Ile_{146} \rightarrow Met$, $Phe_{169} \rightarrow Tyr$, $Pro_{192} \rightarrow Gly$, $Ile_{201} \rightarrow Leu$, $Asn_{236}Asn_{237} \rightarrow AspAsp$, $Glu_{239} \rightarrow Asp$, $Ser_{256} \rightarrow Tyr$, $Val_{268} \rightarrow Phe$, $Lys_{285} \rightarrow Gln$, $Thr_{294} \rightarrow Ser$, and $Leu_{324} \rightarrow Ser$.

14. A vector comprising the nucleic acid molecule of claim 13.

15. A host cell comprising the vector of claim 14.

16. An isolated nucleic acid molecule comprising a nucleic acid sequence encoding a sDAF variant comprising one or more amino acid substitutions within the amino acid sequence shown in FIGS. 2A–E (SEQ ID NO: 4) or an antigenic fragment thereof, wherein said amino acid substitutions are selected from the group consisting of $Lys_{352} \rightarrow Gln$, $Cys_{339} \rightarrow Ser$, $Arg_{394} \rightarrow His$, and $Leu_{403}Phe_{404}Leu_{405} \rightarrow SerTyrSer$.

17. A vector comprising the nucleic acid molecule of claim 16.

18. A host cell comprising the vector of claim 17.

19. An isolated nucleic acid molecule comprising a nucleic acid sequence encoding a DAF variant comprising one or more amino acid insertions in the amino acid sequence shown in FIGS. 1A–D (SEQ ID NO:2) or FIGS. 2A–E (SEQ ID NO:4) or an antigenic fragment thereof, wherein said amino acid insertions are selected from the group consisting of LeuLeu inserted between $Thr_{329}$ and $Cys_{330}$; His inserted between $Arg_{100}$ and $Arg_{101}$; Gln inserted between $Lys_{125}$ and $Lys_{126}$ and Gln inserted between $Lys_{126}$ and $Lys_{127}$; LeuLeu inserted between $Pro_{193}$ and $Ala_{*194}$; AspAsp inserted between $Pro_{247}$ and $Glu_{248}$; SerSer inserted between $Thr_{282}$ and $Thr_{283}$; ThrThr inserted between $Gly_{316}$ and $Thr_{317}$; and N-terminal methionyl.

20. The isolated nucleic acid molecule of claim 19, wherein the amino acid insertions comprise Gln inserted between $Lys_{125}$ and $Lys_{126}$ and Gln inserted between $Lys_{126}$ and $Lys_{127}$.

21. A vector comprising the nucleic acid molecule of claim 19.

22. A host cell comprising the vector of claim 21.

* * * * *

UNITED STATES PATENT AND TRADEMARK OFFICE
CERTIFICATE OF CORRECTION

PATENT NO. : 6,632,634 B1
DATED : October 14, 2003
INVENTOR(S) : Caras et al.

It is certified that error appears in the above-identified patent and that said Letters Patent is hereby corrected as shown below:

Title page,
Item [73], Assignee, should read

-- Genentech, Inc., South San Francisco, CA (US) and
   New York University, New York, NY (US) --
Item [56], References Cited, U.S. PATENT DOCUMENTS, -- 5,324,548 -- should replace "5,374,548"
Item [63], Related U.S. Application Data, filing date for "06/859,107" should be -- May 2, 1986 -- in place of "May 1, 1986"

Column 26,
Line 26, change the number "4" (two occurrences) to arrows

Signed and Sealed this

Twenty-sixth Day of October, 2004

JON W. DUDAS
*Director of the United States Patent and Trademark Office*